(12) United States Patent
Olson et al.

(10) Patent No.: US 8,457,758 B2
(45) Date of Patent: *Jun. 4, 2013

(54) ALIGNMENT INDICATION FOR TRANSCUTANEOUS ENERGY TRANSFER

(75) Inventors: David P. Olson, Minnetrista, MN (US); Andrew L. Schmeling, River Falls, WI (US); Steve J. Nelson, Wyoming, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/210,852

(22) Filed: Aug. 16, 2011

(65) Prior Publication Data

US 2011/0301669 A1 Dec. 8, 2011

Related U.S. Application Data

(60) Continuation of application No. 12/827,304, filed on Jun. 30, 2010, now Pat. No. 8,024,047, which is a division of application No. 11/119,361, filed on Apr. 29, 2005, now Pat. No. 7,774,069.

(51) Int. Cl.
*A61N 1/08* (2006.01)

(52) U.S. Cl.
USPC .......................................................... 607/61

(58) Field of Classification Search
USPC ..................................................... 607/33, 61
See application file for complete search history.

(56) References Cited

U.S. PATENT DOCUMENTS

| | | | |
|---|---|---|---|
| 3,357,434 A | 12/1967 | Abell | |
| 3,824,129 A | 7/1974 | Fagan, Jr. | |
| 3,867,950 A | 2/1975 | Fischell | |
| 3,888,260 A | 6/1975 | Fischell | |
| 4,014,346 A | 3/1977 | Brownlee et al. | |
| 4,041,955 A | 8/1977 | Kelly et al. | |
| 4,071,032 A | 1/1978 | Schulman | |
| 4,082,097 A | 4/1978 | Mann et al. | |
| 4,134,408 A | 1/1979 | Brownlee et al. | |
| 4,186,749 A | 2/1980 | Fryer | |

(Continued)

FOREIGN PATENT DOCUMENTS

| | | |
|---|---|---|
| EP | 0 499 939 B1 | 2/1992 |
| EP | 0 811 395 A3 | 12/1997 |

(Continued)

OTHER PUBLICATIONS

Medtronic, Inc. "Implantable Neurostimulation Systems", 1998.

(Continued)

*Primary Examiner* — Eric D. Bertram
(74) *Attorney, Agent, or Firm* — IPLM Group, P.A.

(57) ABSTRACT

System for transcutaneous energy transfer. An implantable medical device, adapted to be implanted in a patient, has componentry for providing a therapeutic output. The implantable medical device has an internal power source and a secondary coil operatively coupled to the internal power source. An external power source, having a primary coil, provides energy to the implantable medical device when the primary coil of the external power source is placed in proximity of the secondary coil of the implantable medical device and thereby generates a current in the internal power source. An alignment indicator reports the alignment as a function of the current generated in the internal power source with a predetermined value associated with an expected alignment between the primary coil and secondary coil.

12 Claims, 16 Drawing Sheets

U.S. PATENT DOCUMENTS

| | | | |
|---|---|---|---|
| 4,665,896 A | 5/1987 | LaForge et al. |
| 5,279,292 A | 1/1994 | Baumann et al. |
| 5,314,453 A | 5/1994 | Jeutter |
| 5,314,457 A | 5/1994 | Jeutter et al. |
| 5,350,413 A | 9/1994 | Miller |
| 5,411,537 A | 5/1995 | Munshi et al. |
| 5,527,348 A | 6/1996 | Winkler et al. |
| 5,562,714 A | 10/1996 | Grevious |
| 5,613,935 A | 3/1997 | Jarvik |
| 5,690,693 A | 11/1997 | Wang et al. |
| 5,702,431 A | 12/1997 | Wang et al. |
| 5,713,939 A | 2/1998 | Nedungadi et al. |
| 5,733,313 A | 3/1998 | Barreras, Sr. et al. |
| 5,749,909 A | 5/1998 | Schroeppel et al. |
| 5,861,019 A | 1/1999 | Sun et al. |
| 5,876,425 A * | 3/1999 | Gord et al. ............... 607/56 |
| 5,991,664 A | 11/1999 | Seligman |
| 5,991,665 A | 11/1999 | Wang et al. |
| 5,995,874 A | 11/1999 | Borza |
| 6,009,878 A | 1/2000 | Weijand et al. |
| 6,058,330 A | 5/2000 | Borza |
| 6,067,474 A | 5/2000 | Schulman et al. |
| 6,088,619 A | 7/2000 | Hein et al. |
| 6,154,677 A | 11/2000 | Leysieffer |
| 6,178,353 B1 | 1/2001 | Griffith et al. |
| 6,212,431 B1 | 4/2001 | Hahn et al. |
| 6,227,204 B1 | 5/2001 | Baumann et al. |
| 6,275,737 B1 | 8/2001 | Mann |
| 6,308,101 B1 | 10/2001 | Faltys et al. |
| 6,324,430 B1 | 11/2001 | Zarinetchi et al. |
| 6,505,077 B1 | 1/2003 | Kast et al. |
| 6,516,227 B1 | 2/2003 | Meadows et al. |
| 6,553,263 B1 | 4/2003 | Meadows et al. |
| 2001/0045785 A1 | 11/2001 | Wilkerson et al. |
| 2002/0128690 A1 | 9/2002 | Zarinetchi et al. |
| 2003/0014090 A1 | 1/2003 | Abrahamson |
| 2005/0245996 A1 | 11/2005 | Phillips et al. |

FOREIGN PATENT DOCUMENTS

| | | |
|---|---|---|
| EP | 1 048 324 A2 | 11/2000 |
| WO | WO 98/37926 | 9/1998 |
| WO | WO 99/06108 | 2/1999 |
| WO | WO 99/44684 | 9/1999 |
| WO | WO 00/01442 | 1/2000 |
| WO | WO 01/83029 A1 | 11/2001 |
| WO | WO 01/97908 A3 | 12/2001 |

OTHER PUBLICATIONS

Sinha, Gunjan, "The Heart, Medicine & Health", Popular Science, p. 43, Feb. 2000.

Medtronic, Inc. "Mattrix Neurostimulation System", Brochure, 1995.

7-246243, 7-299150, 10-258129, published Abstract of Japanese Applications, 1 pg.

International Search Report and Written Opinion for PCT-US2006-006113.

European Search Report for EP10006610.9.

* cited by examiner

ALIGNMENT INDICATION FOR TRANSCUTANEOUS ENERGY TRANSFER

RELATED APPLICATION

This application is a continuation application of U.S. patent application Ser. No. 12/827,304, filed Jun. 30, 2010, now U.S. Pat. No. 8,024,047, which is a division of U.S. patent application Ser. No. 11/119,361, filed Apr. 29, 2005, now U.S. Pat. No. 7,774,069, and claims priority therefrom.

FIELD OF THE INVENTION

This invention relates to implantable medical devices and, in particular, to energy transfer devices, systems and methods for implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function whether it be driving an electrical infusion pump, providing an electrical neurostimulation pulse or providing an electrical cardiac stimulation pulse. This electrical power is derived from a power source.

Typically, a power source for an implantable medical device can take one of two forms. The first form utilizes an external power source that transcutaneously delivers energy via wires or radio frequency energy. Having electrical wires which perforate the skin is disadvantageous due, in part, to the risk of infection. Further, continuously coupling patients to an external power for therapy is, at least, a large inconvenience. The second form utilizes single cell batteries as the source of energy of the implantable medical device. This can be effective for low power applications, such as pacing devices. However, such single cell batteries usually do not supply the lasting power required to perform new therapies in newer implantable medical devices. In some cases, such as an implantable artificial heart, a single cell battery might last the patient only a few hours. In other, less extreme cases, a single cell unit might expel all or nearly all of its energy in less than a year. This is not desirable due to the need to explant and re-implant the implantable medical device or a portion of the device. One solution is for electrical power to be transcutaneously transferred through the use of inductive coupling. Such electrical power or energy can optionally be stored in a rechargeable battery. In this form, an internal power source, such as a battery, can be used for direct electrical power to the implanted medical device. When the battery has expended, or nearly expended, its capacity, the battery can be recharged transcutaneously, via inductive coupling from an external power source temporarily positioned on the surface of the skin.

Several systems and methods have been used for transcutaneously inductively recharging a rechargeable used in an implantable medical device.

PCT Patent Application No. WO 01/83029 A1, Torgerson et al, Battery Recharge Management For an Implantable Medical Device, (Medtronic, Inc.) discloses an implantable medical device having an implantable power source such as a rechargeable lithium ion battery. The implantable medical device includes a recharge module that regulates the recharging process of the implantable power source using closed-loop feedback control. The recharging module includes a recharge regulator, a recharge measurement device monitoring at least one recharge parameter, and a recharge regulation control unit for regulating the recharge energy delivered to the power source in response to the recharge measurement device. The recharge module adjusts the energy provided to the power source to ensure that the power source is being recharged under safe levels.

Transcutaneous energy transfer through the use of inductive coupling involves the placement of two coils positioned in close proximity to each other on opposite sides of the cutaneous boundary. The internal coil, or secondary coil, is part of or otherwise electrically associated with the implanted medical device. The external coil, or primary coil, is associated with the external power source or external charger, or recharger. The primary coil is driven with an alternating current. A current is induced in the secondary coil through inductive coupling. This current can then be used to power the implanted medical device or to charge, or recharge, an internal power source, or a combination of the two.

U.S. Pat. No. 5,713,939, Nedungadi et al, Data Communication System For Control of Transcutaneous Energy Transmission To an Implantable Medical Device, discloses a data communication system for control of transcutaneous energy transmission to an implantable medical device. The implantable medical device has rechargeable batteries and a single coil that is employed both for energy transmission and data telemetry. Control circuitry in the implantable device senses battery voltage and current through the battery, encodes those values by the use of multiplexer, and transmits the sensed and encoded values through the coil to an external energy transmission device. The external device includes a coil that is electromagnetically coupled to the coil in the implantable device for receiving the encoded signals and for transmitting energy to the implantable device. The external device decodes the transmitted values and transmits those to a controller for controlling energy transmission.

U.S. Pat. No. 6,212,431, Hahn et al, Power Transfer Circuit For Implanted Devices, discloses an external power transfer circuit which couples ac power having a fixed frequency into an implantable electrical circuit, e.g., an implantable tissue stimulator, while automatically maintaining optimum power transfer conditions. Optimum power transfer conditions exist when there is an impedance match between the external and implanted circuits. The external transfer circuit includes a directional coupler and an impedance matching circuit. The directional coupler senses the forward power being transferred to the implant device, as well as the reverse power being reflected form the implant device (as a result of an impedance mismatch). The impedance matching circuit includes at least one variable element controlled by a control signal. The sensed reverse power is used as a feedback signal to automatically adjust the variable element in the impedance matching circuit, and hence the output impedance of the external power transfer circuit, so that it matches the input impedance of the implant device, despite variations that occur in the input impedance of the implant device due to variations in implant distance and implant load.

For implanted medical devices, the efficiency at which energy is transcutaneously transferred is crucial. First, the inductive coupling, while inductively inducing a current in the secondary coil, also has a tendency to heat surrounding components and tissue. The amount of heating of surrounding tissue, if excessive, can be deleterious. Since heating of surrounding tissue is limited, so also is the amount of energy transfer which can be accomplished per unit time. The higher the efficiency of energy transfer, the more energy can be transferred while at the same time limiting the heating of surrounding components and tissue. Second, it is desirable to limit the amount of time required to achieve a desired charge, or recharge, of an internal power source. While charging, or recharging, is occurring the patient necessarily has an external encumbrance attached to their body. This attachment may impair the patient's mobility and limit the patient's comfort. The higher the efficiency of the energy transfer system, the faster the desired charging, or recharging, can be accomplished limiting the inconvenience to the patient. Third, amount of charging, or recharging, can be limited by the amount of time required for charging, or recharging. Since the patient is typically inconvenienced during such charging, or recharging, there is a practical limit on the amount of time during which charging, or recharging, should occur. Hence, the size of the internal power source can be effectively limited by the amount of energy which can be transferred within the amount of charging time. The higher the efficiency of the energy transfer system, the greater amount of energy which can be transferred and, hence, the greater the practical size of the internal power source. This allows the use of implantable medical devices having higher power use requirements and providing greater therapeutic advantage to the patient and/or extends the time between charging effectively increasing patient comfort.

Alignment of an external primary coil with the internal secondary coil is important in achieving efficiency in transcutaneous energy transfer. However, it is not always easy for the user to know when the primary and secondary coils are properly aligned. Often the user must resort to tactile information gleaned from the physical package into which the primary coil is located and a subtle protrusion under the skin approximately where the implantable medical device has been implanted. However, even perfectly aligning the physical package containing the primary coil with the protrusion of the implanted medical device may not result in optimum alignment of the primary and secondary coils. Often the primary coil or the secondary coil, or both, is not centered in the physical packages within which they are contained. Thus, even perfect alignment of the packages may result in actual misalignment of the primary and secondary coils.

BRIEF SUMMARY OF THE INVENTION

Various aspects of the present invention provide a system for transcutaneous energy transfer, external power system for transcutaneous energy transfer or a method for indicating alignment between an external primary coil and an implanted secondary coil. Alternatively, the present invention provides a system for transcutaneous energy transfer having an external power source which varies its power output in order to generate a predetermined current in the internal power source, which can be a function of alignment between the coils, without actually indicating alignment to a user or other person, e.g., a medical professional assisting or performing the transcutaneous energy transfer.

In one embodiment, the present invention provides a system for transcutaneous energy transfer. An implantable medical device, adapted to be implanted in a patient, has componentry for providing a therapeutic output. The implantable medical device has an internal power source and a secondary coil operatively coupled to the internal power source. An external power source, having a primary coil, provides energy to the implantable medical device when the primary coil of the external power source is placed in proximity of the secondary coil of the implantable medical device and thereby generates a current in the internal power source. An alignment indicator reports the alignment as a function of the current generated in the internal power source with a predetermined value associated with an expected alignment between the primary coil and secondary coil.

In a preferred embodiment, the alignment indicator ceases reporting of the alignment following reaching a predetermined point of a charging cycle.

In a preferred embodiment, the predetermined point of a charging cycle comprises following the internal power source reaching a predetermined voltage.

In a preferred embodiment, the predetermined voltage is at least ninety percent of a voltage representing an expected full charge of the internal power source.

In a preferred embodiment, the external power source varies its power output in order to generate a predetermined current in the internal power source.

In another embodiment, the present invention provides an external power system for transcutaneous energy transfer to an implantable medical device, implantable medical device adapted to be implanted in a patient, having componentry for providing a therapeutic output and a secondary coil operatively coupled to the componentry. A primary coil provides energy to the implantable medical device when the primary coil is placed in proximity of the secondary coil of the implantable medical device and thereby generates a current in the internal power source. An alignment indicator reports the alignment as a function of the current generated in the internal power source with a predetermined value associated with an expected alignment between the primary coil and secondary coil.

In a preferred embodiment, the internal power source has an internal impedance and wherein the predetermined value is adjusted as a function of the internal impedance of the internal power source.

In a preferred embodiment, the internal power has a voltage and wherein the predetermined value is adjusted as a function of the voltage of the internal power source.

In a preferred embodiment, the predetermined value decreases as the voltage of the power source decreases.

In a preferred embodiment, the alignment indicator comprises a display.

In a preferred embodiment, the display comprises a percentage of the current generated in the secondary coil to the predetermined value.

In a preferred embodiment, the display comprises a bar graph.

In a preferred embodiment, the expected alignment comprises perfect alignment.

In another embodiment, the present invention provides a system for transcutaneous energy transfer. An implantable medical device, adapted to be implanted in a patient, has componentry for providing a therapeutic output, an internal power source and a secondary coil operatively coupled to the internal power source, the implantable medical device. An external power source, having a primary coil, provides energy to the implantable medical device when the primary coil of the external power source is placed in proximity of the secondary coil of the implantable medical device and thereby generates a current in the internal power source. The external power source varies its power output in order to generate a predetermined current in the internal power source.

In a preferred embodiment, the predetermined current in the internal power source varies as a function of the voltage of the internal power source.

In another embodiment, the present invention provides a method of indicating an alignment between an external primary coil and an inductively coupled secondary coil of an implanted medical device, the secondary coil supplying power to a power source having an internal impedance. The external primary coil is driven with a charging signal. A current generated in the power source by the charging signal is measured. An amount of the current generated in the power source is compared with a predetermined value associated with an expected alignment between the external primary coil and the secondary coil. An amount of the current generated in the power source is compared with a predetermined value. The alignment is reported as a function of the current generated in the secondary coil with the predetermined value from the comparison step. The predetermined value is adjusted as a function of the internal impedance of the power source.

In a preferred embodiment, the steps are repeated as the voltage of the power source declines.

In a preferred embodiment, the power source is a battery.

In a preferred embodiment, the comparing step determines a percentage of the current generated in the secondary coil to the predetermined value.

In a preferred embodiment, the reporting step comprises displaying the percentage.

In a preferred embodiment, the displaying step comprises displaying some of a plurality of steps in a bar graph.

In a preferred embodiment, the displaying step displays perfect alignment when the percentage is one hundred percent.

In a preferred embodiment, the internal impedance of the power source increases over time.

In a preferred embodiment, a power output of the external power source is varied in order to generate a predetermined current in the internal power source.

In another embodiment, the present invention provides a method of transcutaneous energy transfer between an external primary coil and an inductively coupled secondary coil of an implanted medical device. The secondary coil supplies power to a power source having an internal impedance. The external primary coil is driven with a charging signal. A current generated in the power by the charging signal is measured. The charging signal is varied in order to generate a predetermined current in the internal power source.

In a preferred embodiment, the method additionally varies the predetermined current in the internal power source as a function of the voltage of the internal power source.

In a preferred embodiment, the predetermined current in the internal power source declines as the voltage of the internal power source increases during a charging cycle.

In a preferred embodiment, the predetermined current in the internal power source comprises a maximum amount current for charging the internal power source.

In a preferred embodiment, the predetermined current in the internal power source declines over time as the internal impedance of the internal power source increases.

DETAILED DESCRIPTION OF THE INVENTION

The entire content of U.S. patent application Ser. No. 12/827,304, filed Jun. 30, 2010, and U.S. patent application Ser. No. 11/119,361, filed Apr. 29, 2005, now U.S. Pat. No. 7,774,069, are hereby incorporated by reference.

Figure 1:
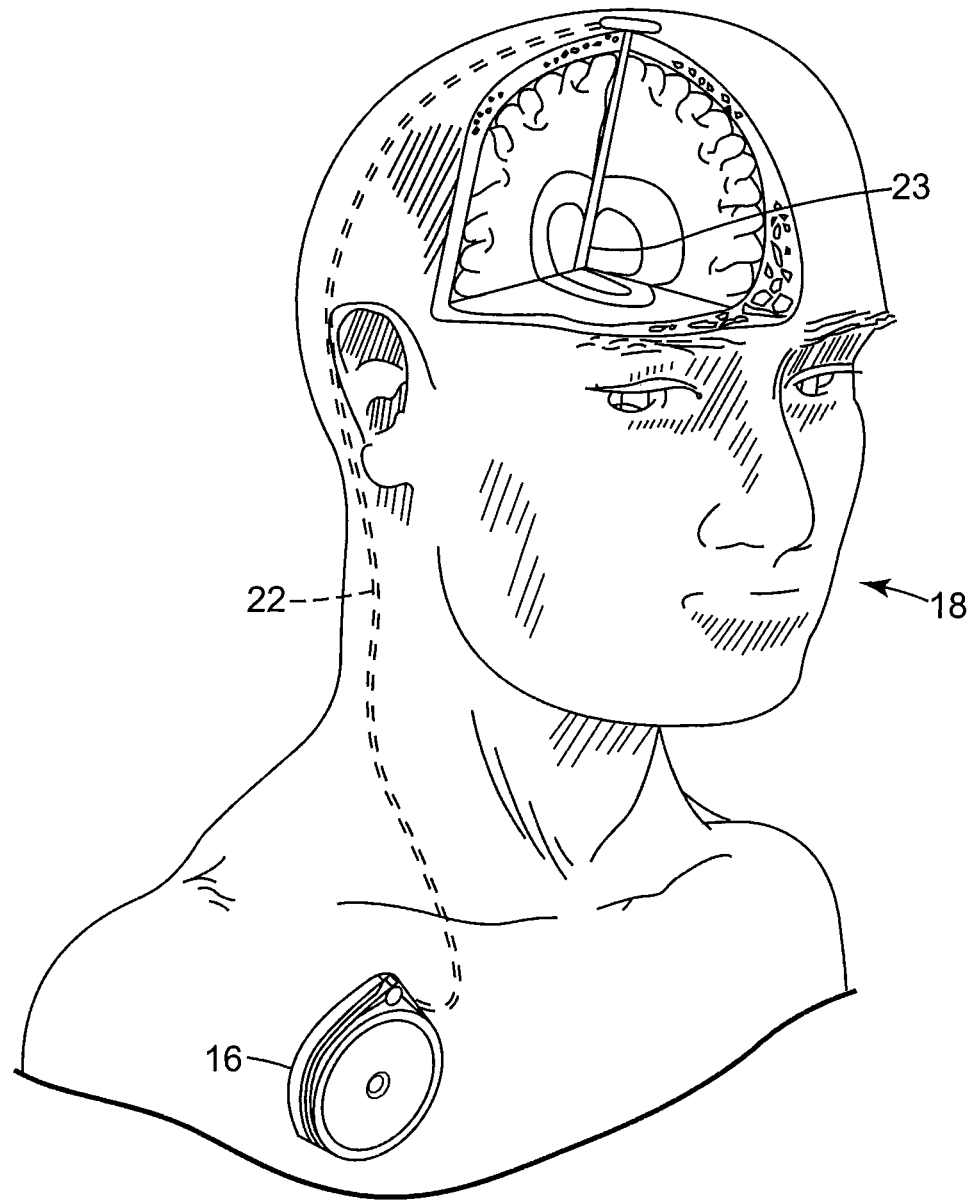
FIG. 1 illustrates an implantable medical device implanted in a patient.

FIG. 1 shows implantable medical device 16, for example, a drug pump, implanted in patient 18. The implantable medical device 16 is typically implanted by a surgeon in a sterile surgical procedure performed under local, regional, or general anesthesia. Before implanting the medical device 16, a catheter 22 is typically implanted with the distal end position at a desired therapeutic delivery site 23 and the proximal end tunneled under the skin to the location where the medical device 16 is to be implanted. Implantable medical device 16 is generally implanted subcutaneously at depths, depending upon application and device 16, of from 1 centimeter (0.4 inches) to 2.5 centimeters (1 inch) where there is sufficient tissue to support the implanted system. Once medical device 16 is implanted into the patient 18, the incision can be sutured closed and medical device 16 can begin operation.

Implantable medical device 16 operates to infuse a therapeutic substance into patient 18. Implantable medical device 16 can be used for a wide variety of therapies such as pain, spasticity, cancer, and many other medical conditions.

The therapeutic substance contained in implantable medical device 16 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

Implantable medical device 16 can be any of a number of medical devices such as an implantable therapeutic substance delivery device, implantable drug pump, cardiac pacemaker, cardioverter or defibrillator, as examples.

Figure 2:
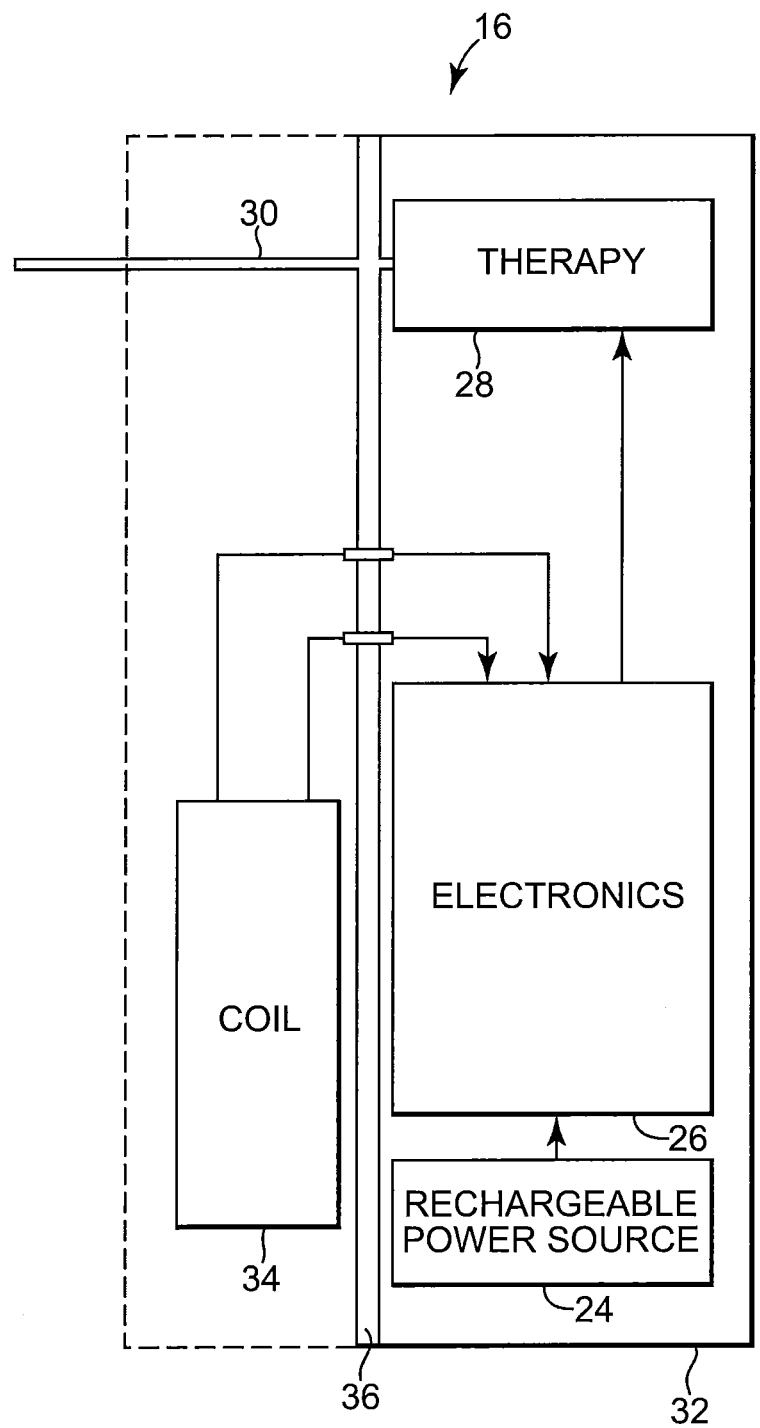
FIG. 2 is a block diagram of an implantable medical device.

In FIG. 2, implantable medical device 16 has a rechargeable power source 24, such as a Lithium ion battery, powering electronics 26 and therapy module 28 in a conventional manner. Therapy module 28 is coupled to patient 18 through one or more therapy connections 30, also conventionally. Rechargeable power source 24, electronics 26 and therapy module 28 are contained in hermetically sealed housing 32. Secondary charging coil 34 is attached to the exterior of housing 32. Secondary charging coil 34 is operatively coupled through electronics 26 to rechargeable power source 24. In an alternative embodiment, secondary charging coil 34 could be contained in housing 32 or could be contained in a separate housing umbilically connected to electronics 26. Electronics 26 help provide control of the charging rate of rechargeable power source 24 in a conventional manner. Magnetic shield 36 is positioned between secondary charging coil 34 and housing 32 in order to protect rechargeable power source 24, electronics 26 and therapy module 28 from electromagnetic energy when secondary charging coil 34 is utilized to charge rechargeable power source 24.

Rechargeable power source 24 can be any of a variety power sources including a chemically based battery or a capacitor. Rechargeable power source may be a well known lithium ion battery.

Figure 3:
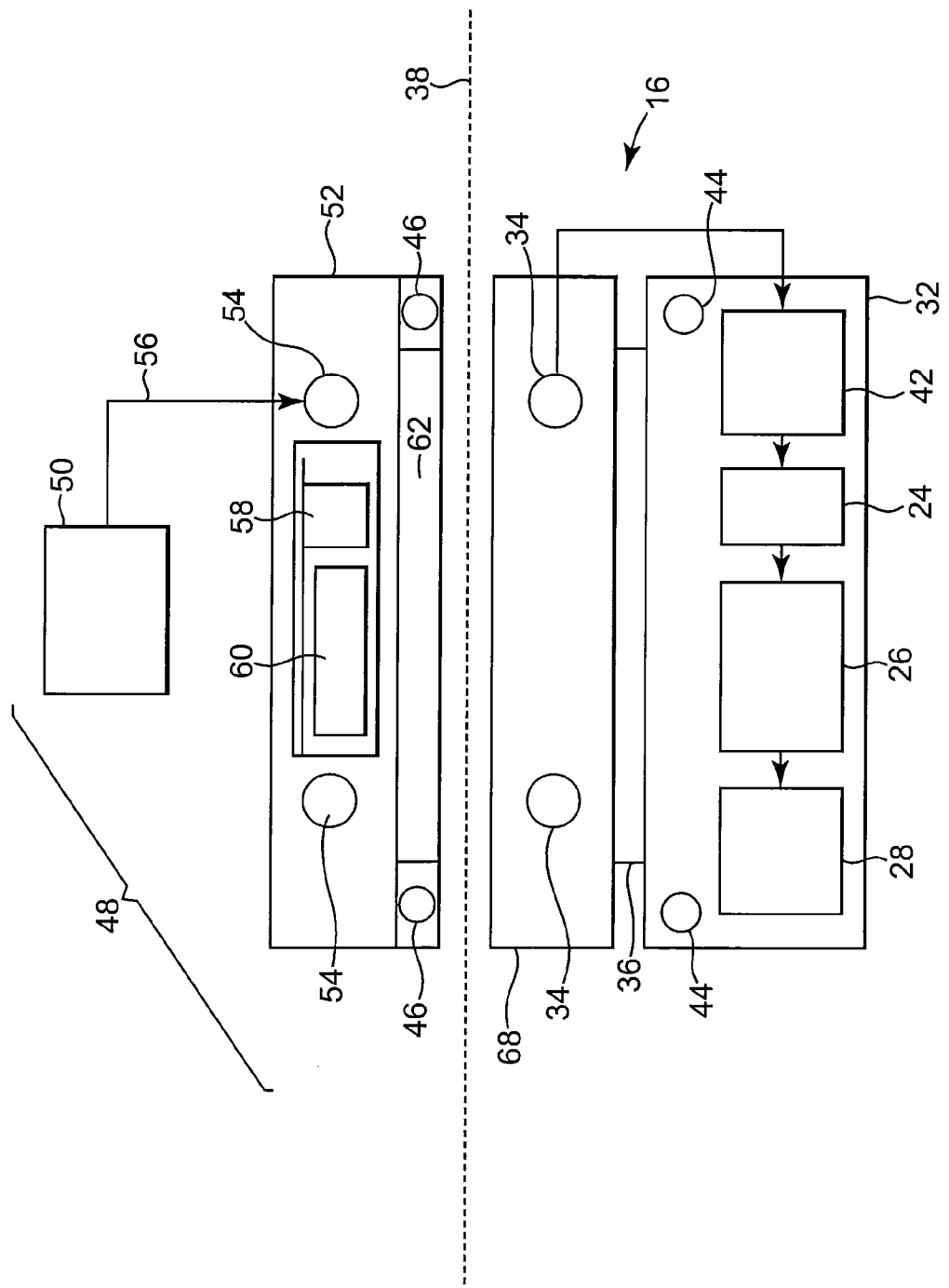
FIG. 3 is a detailed block diagram of an implantable medical device implanted subcutaneously and an associated external charging device in accordance with an embodiment of the present invention.

FIG. 3 illustrates an alternative embodiment of implantable medical device 16 situated under cutaneous boundary 38. Implantable medical device 16 is similar to the embodiment illustrated in FIG. 2. However, charging regulation module 42 is shown separate from electronics 26 controlling therapy module 28. Again, charging regulation and therapy control is conventional. Implantable medical device 16 also has internal telemetry coil 44 configured in conventional manner to communicate through external telemetry coil 46 to an external programming device (not shown), charging unit 50 or other device in a conventional manner in order to both program and control implantable medical device and to externally obtain information from implantable medical device 16 once implantable medical device has been implanted. Internal telemetry coil 44, rectangular in shape with dimensions of 1.85 inches (4.7 centimeters) by 1.89 inches (4.8 centimeters) constructed from 150 turns of 43 AWG wire, is sized to be larger than the diameter of secondary charging coil 34. Secondary coil 34 is constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 36 is positioned between secondary charging coil 34 and housing 32 and sized to cover the footprint of secondary charging coil 34.

Internal telemetry coil 44, having a larger diameter than secondary coil 34, is not completely covered by magnetic shield 36 allowing implantable medical device 16 to communicate with the external programming device with internal telemetry coil 44 in spite of the presence of magnetic shield 36.

Rechargeable power source 24 can be charged while implantable medical device 16 is in place in a patient through the use of external charging device 48. In an embodiment, external charging device 48 consists of charging unit 50 and external antenna 52. Charging unit 50 contains the electronics necessary to drive primary coil 54 with an oscillating current in order to induce current in secondary coil 34 when primary coil 54 is placed in the proximity of secondary coil 34. Charging unit 50 is operatively coupled to primary coil by cable 56. In an alternative embodiment, charging unit 50 and antenna 52 may be combined into a single unit. Antenna 52 may also optionally contain external telemetry coil 46 which may be operatively coupled to charging unit 50 if it is desired to communicate to or from implantable medical device 16 with external charging device 48. Alternatively, antenna 52 may optionally contain external telemetry coil 46 which can be operatively coupled to an external programming device, either individually or together with external charging unit 48.

As will be explained in more detail below, repositionable magnetic core 58 can help to focus electromagnetic energy from primary coil 46 to more closely be aligned with secondary coil 34. Also as will be explained in more detail below, energy absorptive material 60 can help to absorb heat build-up in external antenna 52 which will also help allow for a lower temperature in implantable medical device 16 and/or help lower recharge times. Also as will be explained in more detail below, thermally conductive material 62 is positioned covering at least a portion of the surface of external antenna 52 which contacts cutaneous boundary 38 of patient 18.

Figure 4:
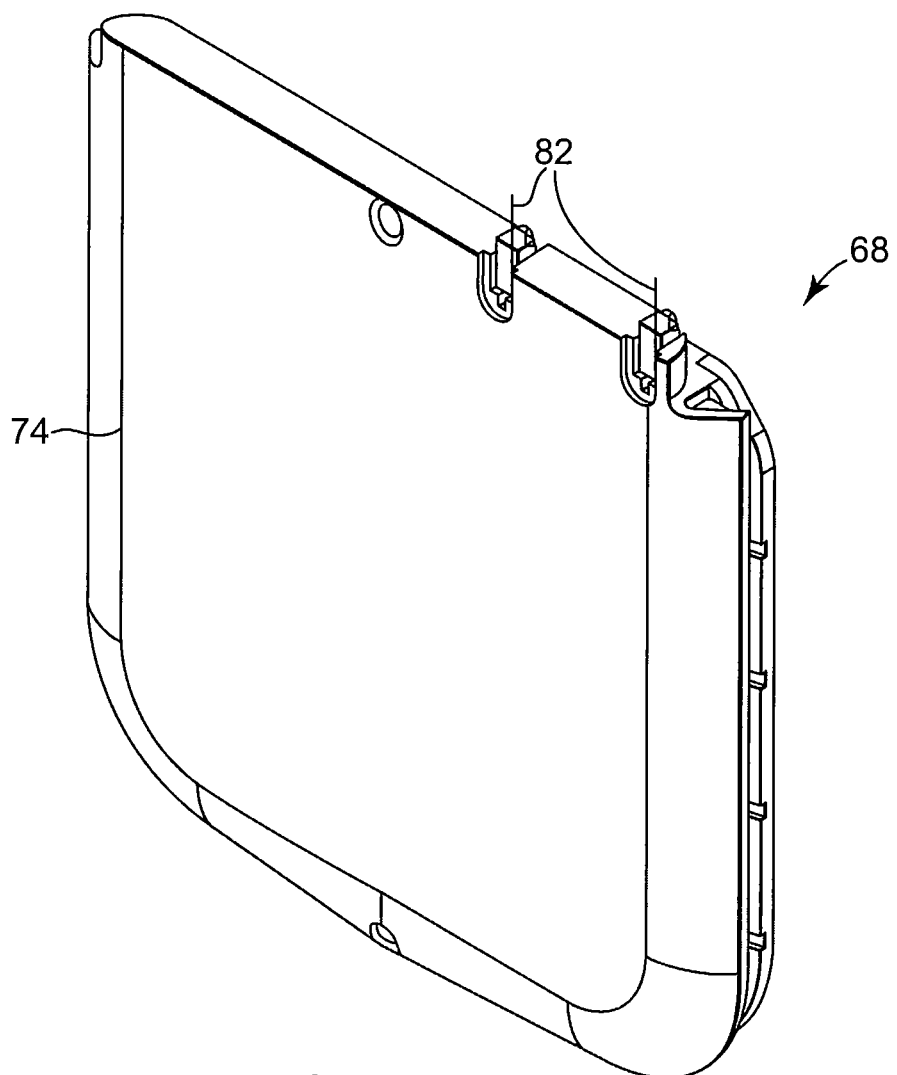
FIG. 4 is a perspective view of an internal antenna associated with an implantable medical device.
Figure 5:
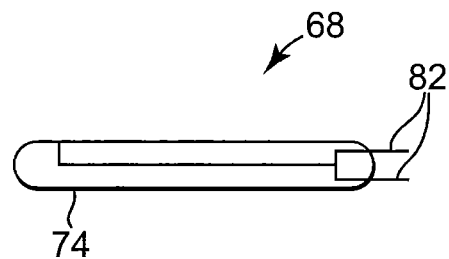
FIG. 5 is a side view of the internal antenna of FIG. 4.

As shown in FIG. 4 and FIG. 5, secondary coil 34 and magnetic shield 36 are separate from but adjacent to housing 32 encompassing the remainder of implantable medical device 16. Internal antenna 68 is contained in a separate housing 74 which is attachable to housing 32 so that implantable medical device 16 can be implanted by a medical professional as essentially one unit. Secondary coil 34 is electrically attached to charging regulation module 42 through leads 82.

In order to achieve efficient inductive coupling between primary coil 54 of external antenna 52 and secondary coil 34, it is desirable to place primary coil 54 of external antenna 52 as close to secondary coil 34 as possible. Typically, external antenna 52 is placed directly on cutaneous boundary 38 and, since the location of implantable medical device 16 is fixed, the distance across cutaneous boundary 38 between primary coil 54 and secondary coil 34 is minimized as long as external antenna 52 is kept adjacent cutaneous boundary 38.

Figure 6:
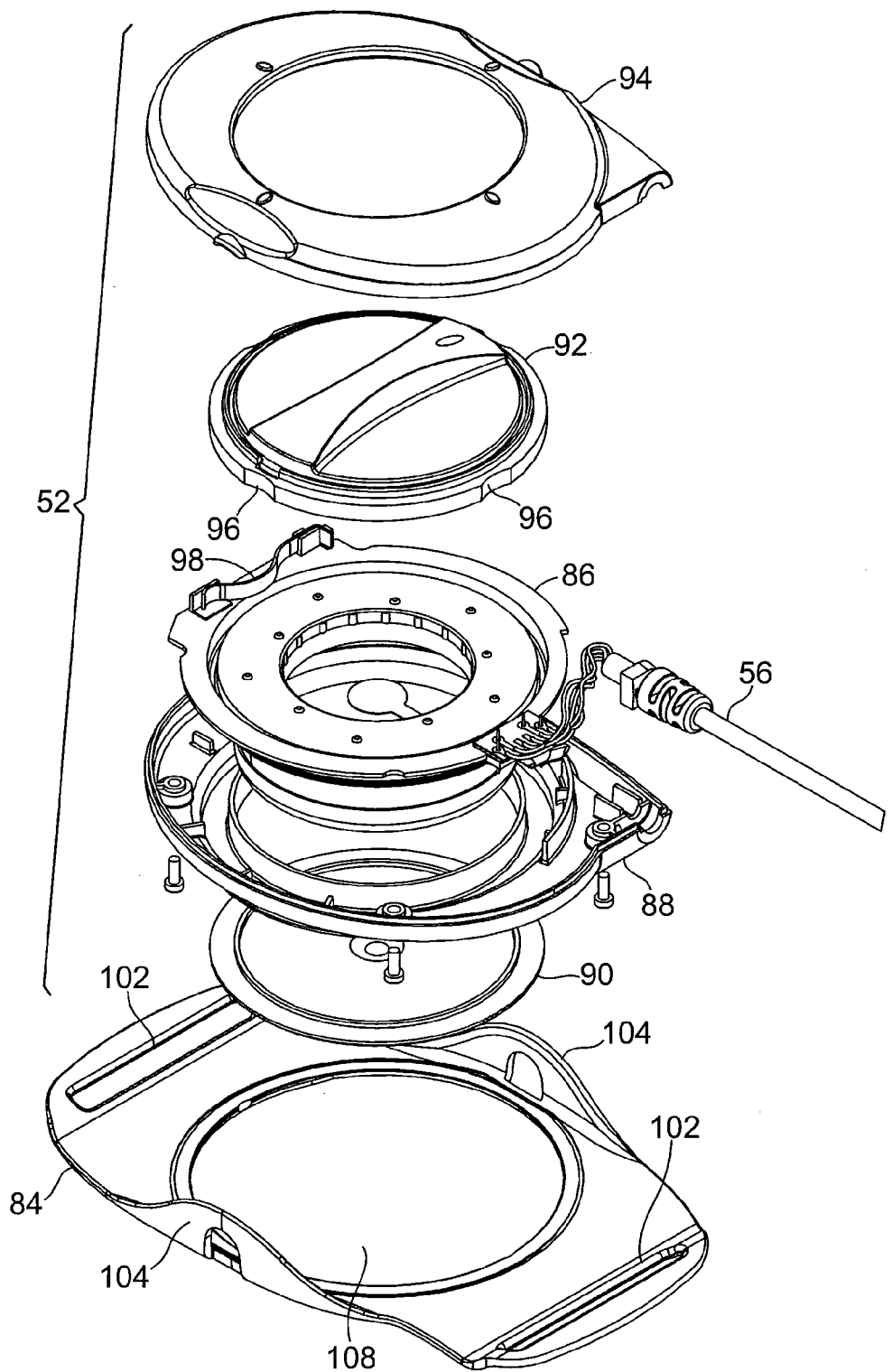
FIG. 6 is an exploded perspective view an external antenna and associated bracket in accordance with an embodiment of the present invention.

External antenna 52 is attachable to patient 18 with bracket 84 when charging rechargeable power source 24. FIG. 6 is an exploded illustration of an embodiment of external antenna 52 attachable to bracket 84. Primary coil 54 is contained in bobbin assembly 86 which sits in bottom housing 88. Primary coil is connectable to cable 56. The bottom of external antenna 52 is formed from a thermally conductive material 90. Rotating core cup assembly 92 is held in place by top housing 94. Rotating core cup assembly 92 is rotatable is allowed to rotate within external antenna 52. Detents 96 engage detent spring 98 to position rotatable core cup assembly 92 in one of a plurality of detent positions. External antenna may be secured together, for example, with screws (not shown) holding top housing 94 and thermally conductive material 90 together.

Bracket 84 is adapted to be attached to the body of patient 18 with a belt (not shown) attachable to bracket 84 with belt loops 102. Ears 104 are adapted to mate with tabs 106 in top housing 94 and pivotally secure external antenna 52 in bracket 84 when charging is to be accomplished. Bracket 84 has an opening 108 allowing thermally conductive material 90 of external antenna 52 to contact the skin of patient 18 when external antenna 52 is pivotally secured in bracket 84.

As bracket 84 is attached to patient 18 with a belt via belt loops 102, the skin surface of patient 18 is typically not completely flat. For example, if implantable medical device 16 is implantable in the body torso of patient 18, then the belt attached via belt loops 102 will typically pass around the torso of patient 18. Since the torso of patient 18, and especially the torso of patient 18 near the location of implantable medical device 16, bracket 84 may not sit completely flat on patient 18. This may be especially true as patient 18 moves and the torso flexes during such movement. Bracket 84 may be conformal and flexible in order to conform to the shape of the body of patient 18. However, bracket 84 may also be rigid enough so that opening 108 in bracket 84 maintains its shape in order to properly receive external antenna 52. Bracket 84 is preferably constructed of PCABS. To maintain the proper position of bracket 84 with the skin of patient 18, the surface of bracket 84 closest to patient 18 contains material 109 constructed from a high durometer, e.g., 40 Shore A, or "sticky" material such as a material known under the trade name of "Versaflex" manufactured by GLS Corp. of McHenry, Ill. This will help external antenna to sit more closely to the skin surface of patient 18 and remain there during movements of patient 18 throughout the charge or recharge cycle. In addition, external antenna 52 is allowed to pivot by way of ears 104 on tabs 106. Bracket 84 is configured to allow thermally conductive material 90 to extend through opening 108 and contact the skin surface of patient 18. Allowed pivoting of external antenna 52 and, hence, thermally conductive material 90, permits thermally conductive surface to sit more closely to the skin surface of patient 18.

Figure 7:
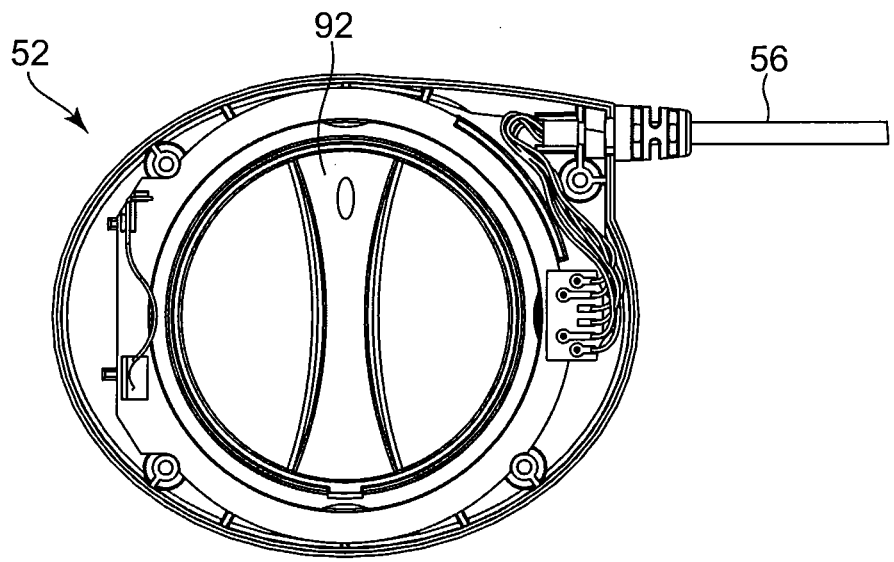
FIG. 7 is a top view of an external antenna in accordance with an embodiment of the present invention.

FIG. 7 is a partially cut away top view of external antenna 52 in assembled form and attached to cable 56. Rotatable core cup assembly 92 is shown located inside of primary coil 54 and positionable in selected rotated positions via detents 96 and detent spring 98. In FIG. 7, rotatable core cup assembly is positioned between with detent spring 98 between detents 96 illustrating that while multiple detent positions are available, rotatable core cup assembly can be positioned between detent positions and, indeed, at any rotated position.

Figure 8:
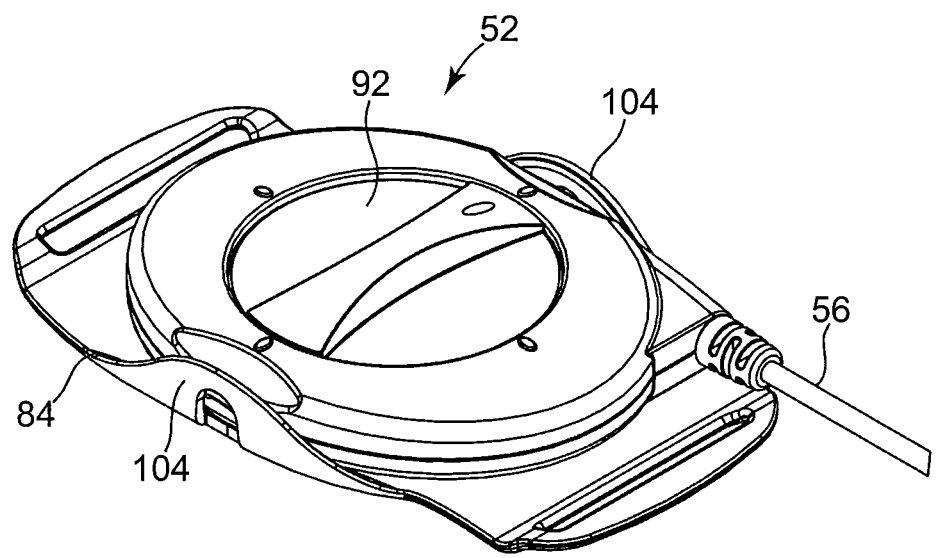
FIG. 8 is a perspective view of an external antenna and bracket combination in accordance with an embodiment of the present invention.

In FIG. 8, the assembly of external antenna 52 with bracket 84 is shown connected to cable 56. Bracket 84 may be affixed to patient 18 through belt loops 102 and then, after bracket 84 has been affixed to patient 18, external antenna 52 be attached to bracket 84. Affixing bracket 84 to patient 18 first allows for bracket 84 to be used to laterally position external antenna close to the position of implantable medical device 16.

Typical prior art positioning systems rely on the external antenna for lateral positioning. The external antenna is moved around on the body of the patient 18 until the best lateral position is found. When the best lateral position is found, the external antenna is removed from the body and the bottom of the external antenna (the portion of the external antenna) contacting the patient's body) is made to be resistant to lateral movement. As an example, one way is to remove a protective liner exposing a sticky surface allowing the external antenna to be relatively fixed in location. However, the very act of lifting the external antenna in order to remove the protective liner and replacing the external antenna on the body of the patient 18 causes crucial positioning information to be lost. There is no guarantee, and in fact it is not likely, that the external antenna will be replaced in the exact same position as the position previously found to be best.

In contrast, bracket 84 of the present invention can be used to roughly find the optimum position for external antenna 52. This can be done relatively easily due to opening 108 in bracket 84. Implantable medical device 16, when implanted, usually leaves an area of the body of patient 18 which is not quite as flat as it was before implantation. That is, implantable medical device 16 usually leaves an area of the skin of patient 18 which bulges somewhat to accommodate the bulk of implantable medical device 16. It is relatively easy for patient, medical professional or other person, to place bracket 84 in the general area of implantable medical device 16 and move bracket 84 around until the bulge caused by implantable medical device 16 is most closely centered in opening 108. As bracket 84 is moved laterally, opening 108 tends to naturally center on the bulge created by implantable medical device 16. Once positioned in this manner, bracket 84 can be secured to the body of patient 18 with belt (not shown) attached via belt loops 102. Securing and/or tightening, by pulling the belt tight or snapping a buckle, for example, can be without removing bracket 84 from the body of patient 16. Thus, bracket 84 can be relatively easily positioned over the general location of implantable medical device 16 and secured in that position without being removed from the body of patient 18.

Figure 9:
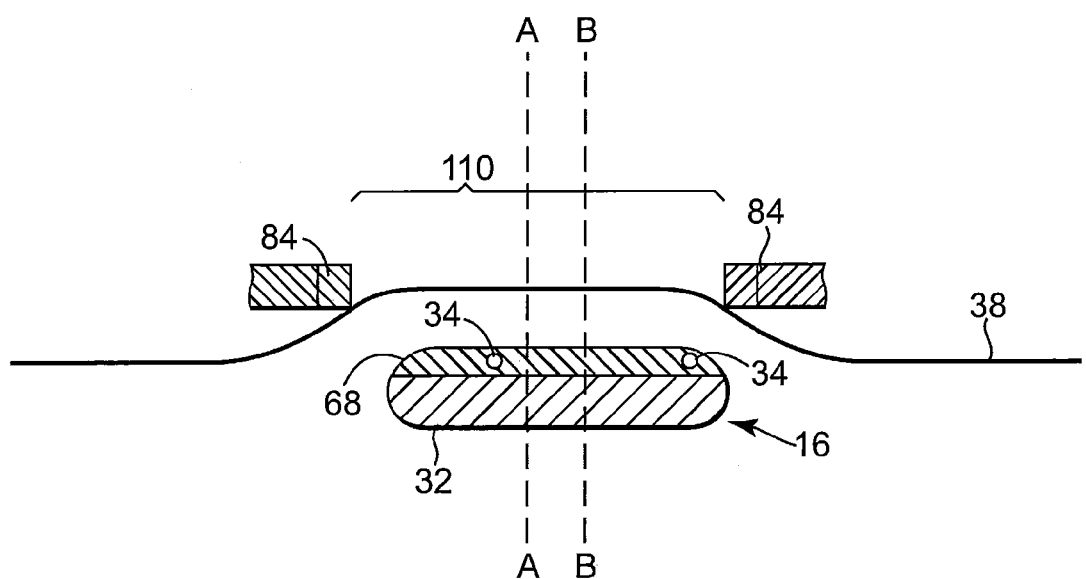
FIG. 9 is a cross-sectional side view of an implantable medical device implanted subcutaneously and an associated bracket for use with an external antenna.

FIG. 9 is cross-sectional view of implantable medical device 16 implanted in patient 18 approximately one centimeter under cutaneous boundary 38 creating bulging area 110, an area of the body of patient 18 in which the skin of patient 18 is caused to bulge slightly due to the implantation of implantable medical device 16. Bulging area 110 is an aid to locating the position of external antenna 52 relative to secondary coil 34. Bracket 84 can be positioned roughly in the area where implantable medical device 16 is implanted. Opening 108 in bracket 84 can aid in establishing the location of implantable medical device. Bracket 84 can be roughly centered over bulging area 110. After external antenna 52 is coupled to bracket 84, then primary coil 54 can be generally centered on implantable medical device 16.

However, secondary coil 34 may not be centered with respect to implantable medical device 16. This can occur due to a variety of reasons such as the need for operatively coupling secondary coil 34 to charging regulation module 42. Connections to make this operative coupling may require physical space on one side of internal antenna 68 which may cause secondary coil 34 not to be centered on implantable medical device 16. It is also possible that the attachment of internal antenna 68 to housing 32 can cause secondary coil 34 not to be centered on implantable medical device 16. Regardless of the cause, if secondary coil 34 is not centered on implantable medical device 16, then centering bracket 84 on bulging area 110 may not optimally position primary coil 54 with respect to secondary coil 34. Any offset in the position of primary coil 54 and secondary coil 34 may not result in the most efficient energy transfer from external antenna 52 to implantable medical device 16.

Figure 10:
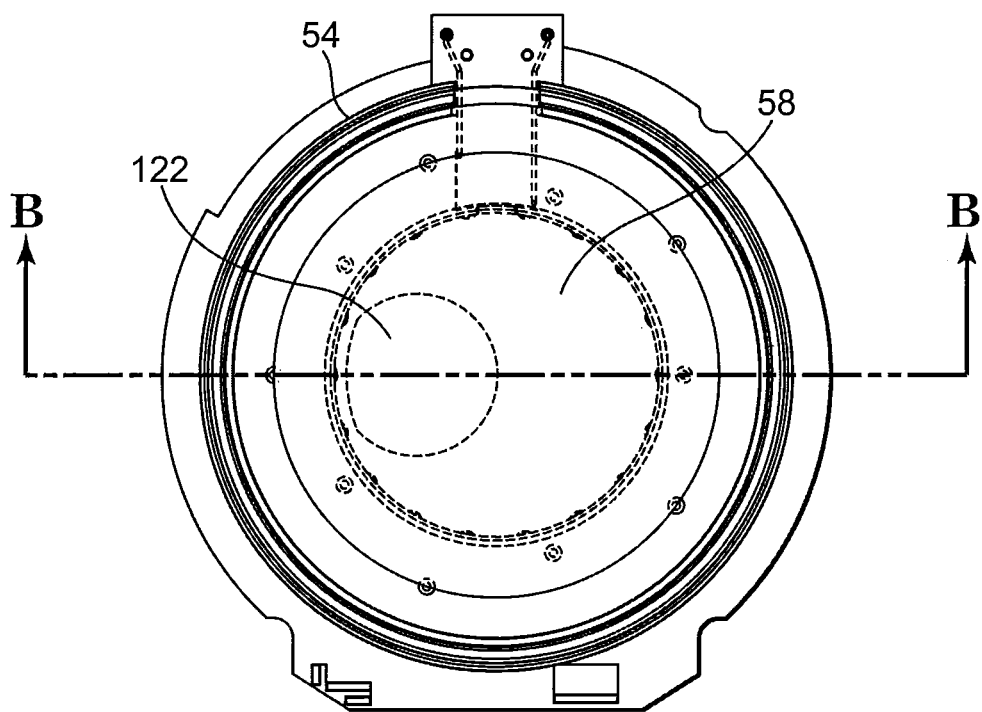
FIG. 10 is a cut-away top view of view a primary coil and associated magnetic core in accordance with an embodiment of the present invention.
Figure 11:
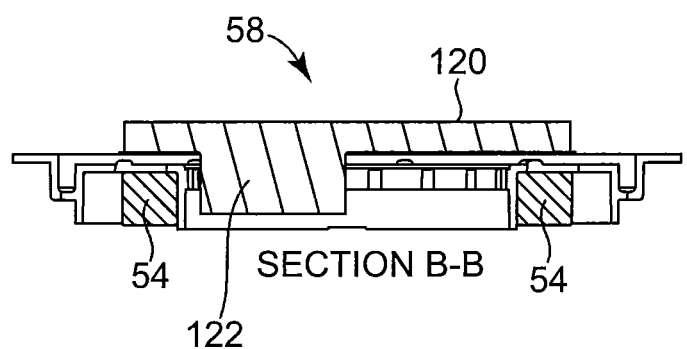
FIG. 11 is a cross-sectional view of the primary coil and associated magnetic core of FIG. 10 taken through section line B-B.

A magnetic core 58 is positioned within primary coil 54 in order to focus energy generated by primary coil 54. Magnetic core 58 attracts the magnetic flux lines generated by primary coil 54. The position of magnetic core 58 within primary coil 54 determines the lateral location of the largest amount of the flux lines generated by primary coil 54. FIGS. 10 and 11 show cut-away top and cross-sectional views of magnetic core 58 used with primary coil 54. Magnetic core 58 is moveable within primary coil 54. Lower portion 122 of magnetic core 58 can be rotated to a plurality of positions within primary coil 58 by rotating core cup assembly 92 (see FIG. 12). The travel path of magnetic core 58 can be locked in a plurality of discrete positions. Magnetic core 58 may be locked in four (4) different positions by detents 96 and detent spring 98 (see FIG. 6). Magnetic core 58 has an upper planar portion 120 and a smaller lower portion 122.

As magnetic core 58 is repositioned within primary coil 54, the focus of magnetic flux generated by primary coil 54 is also repositioned. As noted above, external antenna 52 is generally aligned with implanted medical device 16 using palpatory sensation. Moveable magnetic core 58 can then be used to provide a "fine" adjustment to the lateral positioning of external antenna 52 with respect to secondary coil 34. After bracket 84 has been secured to patient 18, external antenna 52 is attached to bracket 84. Magnetic core 58 is then moved until the best lateral alignment with secondary coil 34.

Figure 12:
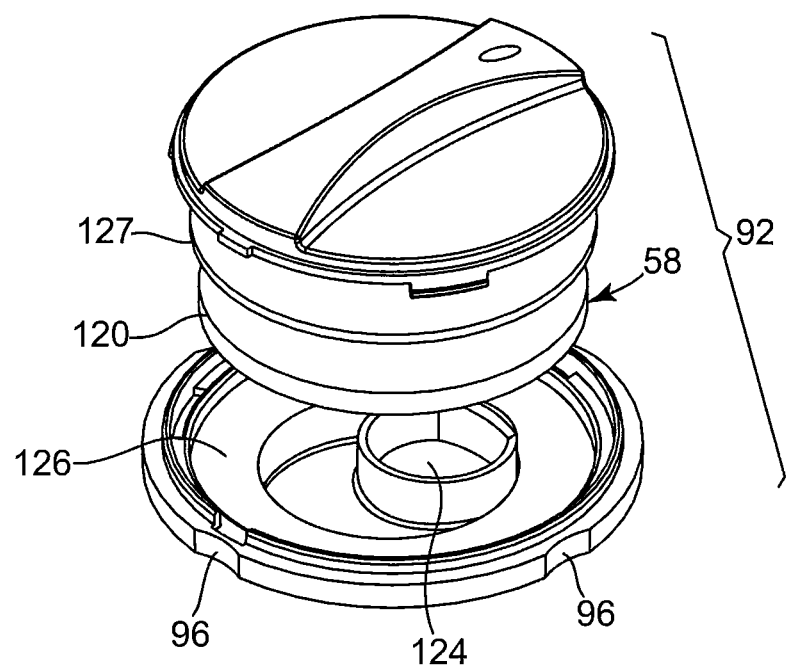
FIG. 12 is an exploded view a portion of an external antenna constructed in accordance with an embodiment of the present invention showing the magnetic core and a core cup assembly.

Magnetic core 58 is shown positioned within external antenna 52 of FIG. 12. Core cup assembly 92 holds magnetic core 58 within the assembly of external antenna 52. Lower portion 122 (not visible in FIG. 12) of magnetic core 58 fits into recess 124 of core cup assembly 92 while upper portion 120 of magnetic core 58 rests upon ledge 126 of core cup assembly 92. Preferably, magnetic core 58 is a ferrite core. Still more preferably, magnetic core 58 is constructed from MN60LL high performance, low loss ferrite manufactured by Ceramic Magnetics, Inc., Fairfield, N.J. Magnetic core 58 has an initial permeability of 6,500 and a maximum permeability of 10,500 (typical) with a volume resistivity of 500 ohm-centimeters.

A surface, preferably the top, of magnetic core 58 is lined with an adhesive coated foam 127 and contained in core cup assembly 92. Magnetic core 58 has a tendency to be brittle. Containing magnetic core 58 in core cup assembly assures that even if magnetic core 58 has one or more fractures, magnetic core 58 will still be properly positioned and continue to function. Foam 127 also helps to hold magnetic core 58 together and minimize gaps between fractured segments of magnetic core 58. Further, foam 127 adds mechanical stability to magnetic core 58 helping to cushion magnetic core 58 against mechanical impacts, such as from dropping external antenna 52 against a hard surface, and helps to prevents audible rattles which may otherwise develop from a fractured magnetic core 58.

Figure 13:
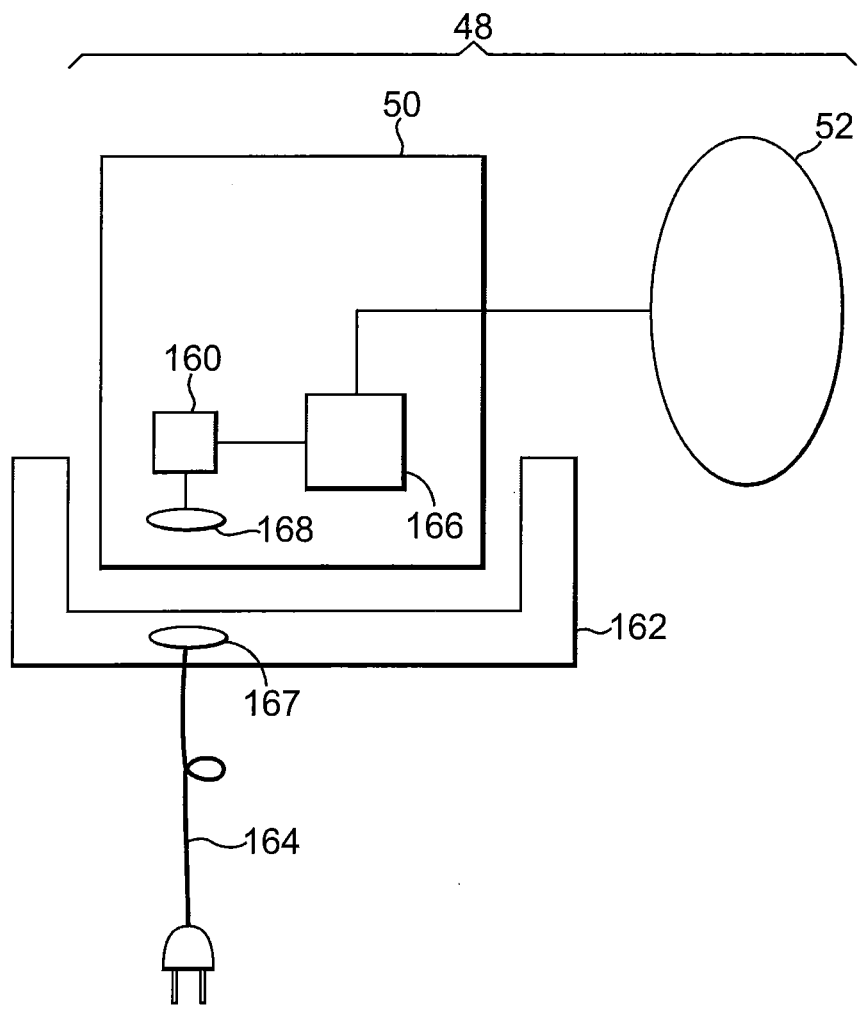
FIG. 13 is block diagram of an external charging unit and an associated inductively coupled cradle for recharging the external charging unit.

As shown in FIG. 13, external charging device 48 can be powered either directly from internal (to charging unit 50) batteries 160 or indirectly from desktop charging device 162. Desktop charging device is connectable via power cord 164 to a source of AC power, such as a standard readily available wall outlet. Desktop charging device 162 can be configured as a cradle which can receive charging unit 50. Other forms of connection from desktop charging device 162 to a power source, such as by a dedicated line cable can also be utilized. Desktop charging device 162 can charge and/or recharge batteries 160 in charging unit 50, preferably by inductive coupling using coil 167 positioned in desktop charging device 162 and coil 168 positioned within charging unit 50. Once charged and/or recharged, batteries 160 can provide the power through internal circuitry 168 and cable 56 to external antenna 52. Since charging unit 50 may not be coupled directly to the line voltage source of AC power, charging unit 50 may be used with external antenna 52 to transfer power and/or charge implanted medical device 16 while desktop charging device 162 is coupled to a line voltage source of AC power. The inductive coupling using coil 167 and coil 168 break the possibility of a direct connection between the line voltage source of AC power and external antenna 52. Batteries 160 also allow charging unit 50 and, hence, external charging device 48, to be used in transferring power and/or charging of implanted medical device 16 while completely disconnected from either a line voltage source of AC power or desktop charging device 162. This, at least in part, allows patient 18 to be ambulatory while transferring power and/or charging implanted medical device 16.

Figure 14:
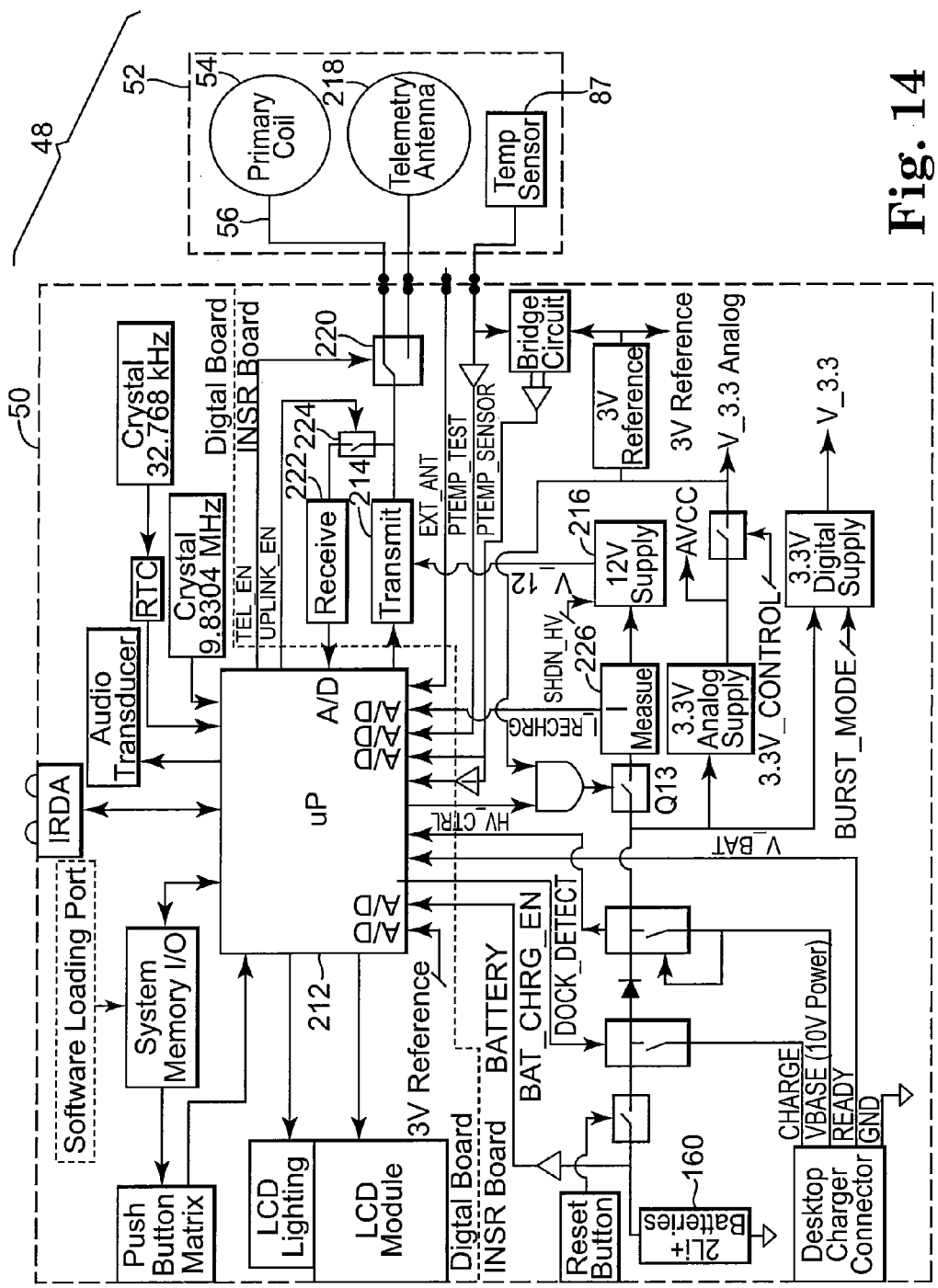
FIG. 14 is a detailed block diagram of the external charging unit of FIG. 13.

FIG. 14 is a block diagram of external charging device 48 controlled by microprocessor 212. Transmit block 214 consists of an H-bridge circuit powered from 12 volt power supply 216. Transmit block 214 drives primary coil 54 in external antenna 52. H-bridge control signals and timing are provided conventionally by microprocessor 212. H-bridge circuit in transmit block 214 is used to drive both primary coil 54, used for power transfer and/or charging, and telemetry antenna 218. Drive selection is done by electronically controllable switch 220. During power transfer and/or charging, H-bridge circuit is driven at 9 kiloHertz. During telemetry, H-bridge circuit is driven at 175 kiloHertz.

Receive block 222 is used only during telemetry, enabled by switch 224, to receive uplink signals from implanted medical device 16. Twelve volt power supply 216 is a switching regulator supplying power to transmit block 214 during power transfer and/or charging as well as telemetry downlink. Nominal input voltage to 12 volt power supply 216 is either 7.5 volts from lithium ion batteries 226 or 10 volts from desktop charging device 162 (FIG. 13).

Current measure block 226 measures current to 12 volt power supply 216. Current measured by current measure block 226 is used in the calculation of power in along with the voltage of batteries 160. As noted above, power in is used in the calculation of efficiency of power transfer and/or charging efficiency to determine, in part, the best location of external antenna 52 and/or rotating core cup assembly 92.

Rotating core cup assembly 92 is rotated in external antenna 52 for better lateral alignment of primary coil 54 and secondary coil 34. A feedback mechanism is used to determine the best rotation of core cup assembly 92. External charging device 48 can determine whether the current position of rotating core cup assembly 92 is optimally aligned for energy transfer and/or charging. External charging device 48 measures the power out of external charging device 48 divided by the power into external charging device 48. This calculation is a measure of the efficiency of external charging device 48. The power out is gauged by the power induced in implantable medical device 16 and is determined by multiplying the voltage of rechargeable power source 24 by the charging current in implantable medical device 16. These values are obtained by telemetry from implanted medical device 16. The power in is gauged by the power generated by charging unit 50 and is determined by multiplying the voltage of the internal voltage of charging unit 50, e.g., the voltage of a battery or batteries internal to charging unit 50, by the current driving external antenna 52, in particular I-recharge from Imeasure unit 226.

The ratio of power out divided by power in can be scaled displayed to patient 18, or a medical professional or other person adjusting rotatable core cup assembly 92 or positioning external antenna 52. For example, the available efficiency can be divided into separate ranges and displayed as a bar or as a series of lights. The separate ranges can be linearly divided or can be logarithmic, for example.

Using efficiency as a measure of effective coupling and, hence, as a measure of proper location of external antenna 52 and rotatable core cup assembly 92 works not only at high charging or power transfer levels but also at reduced charging levels, as for example, when charging at reduced levels toward the end or beginning of a charging cycle.

If, after patient 18 or other person has moved rotatable core cup assembly 92 through all of the range of positions on external antenna 52 and can not achieve an acceptable efficiency level, patient 18 or other person can remove external antenna 52 from bracket 84, realign bracket 84 with bulging area 110, reattach external antenna 52 to bracket 84 and restart the alignment and coupling efficiency process.

Figure 15:
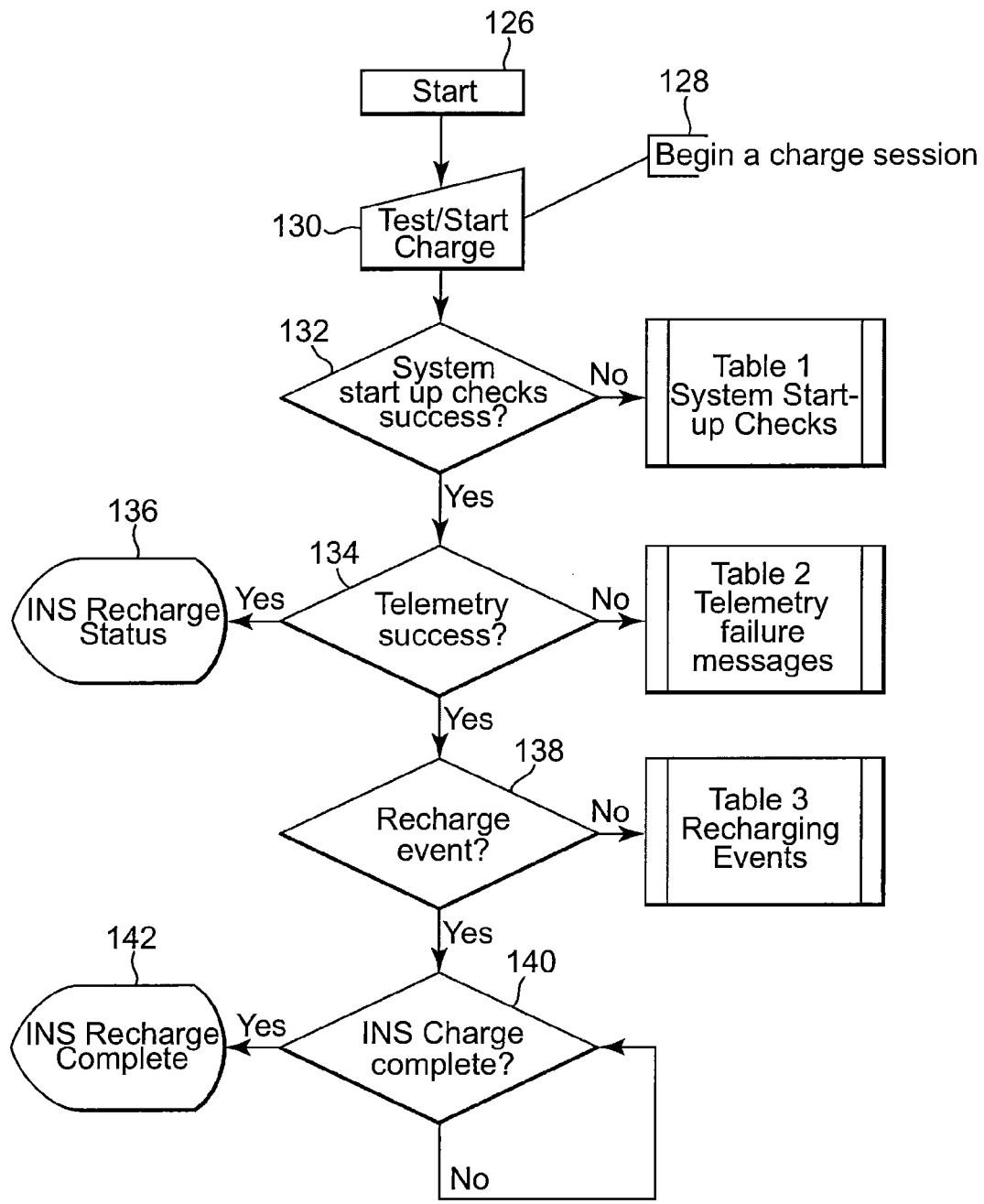
FIG. 15 is a flow chart illustrating a charging process in accordance with an embodiment of the present invention.

FIG. 15 is a flow chart illustrating an exemplary charging process using external antenna 52. The process starts [block 126] and a charging session begins [block 128] with a test [block 130]. The charging system performs start-up checks [block 132]. If the start-up checks are not performed successfully, the actions taken in Table 1 are performed.

TABLE 1

| Check | Screen/Message |
| --- | --- |
| System Errors: e.g., stuck key | System Error |
| External Charger Battery Status | Recharge Complete |
|  | Battery Low |
|  | Recharge External Charger |
| External Charger Connected to External Antenna | Recharge in Process Icon |
| Antenna Disconnect | Connect Antenna |

If the start-up checks are successful, telemetry with implantable medical device 16 is checked [block 134]. If telemetry is unsuccessful, the error messages indicated in Table 2 are generated.

TABLE 2

| Failure | Screen/Message |
| --- | --- |
| Poor Communication | Reposition Antenna |
| External Charger Error Code Response | Call Manufacturer |
| Communication Error | Communication Error |
| External Charger Fault | Call Manufacturer |
| Antenna Disconnect | Connect Antenna |
| Antenna Failure | Antenna Failure Icon |

If telemetry checks are successful, external charging device 48 is able to monitor [block 136] charging status. Monitoring charging status can includes providing feedback to an operator to help determine the best rotational position of core cup assembly 92.

Charge events are checked [block 138]. If no charge events are noted, the actions indicated in Table 3 are executed.

TABLE 3

| Event | Screen/Message |
| --- | --- |
| Telemetry Failure | (See Messages From Table 2) |
| Implantable Medical Device Battery Low | Device Battery Low |
| External Charger Battery Low | Charger Battery Low |
| External Charger Battery Depleted | Recharge Charger |
| External Charger Recharge Complete | External Charger Recharge Complete |
| Implantable Medical Device Will Not Provide Therapeutic Result Until Recharged: Therapy Unavailable/Sleep Mode | Recharge Device |
| Antenna Disconnect | Connect Antenna |

If a charge event occurs, then the process checks to determine if charging is complete [block 140]. Once charging is complete, the process terminates [block 142].

As energy is transferred from primary coil 54 of external antenna 52 to secondary coil 34 of implantable medical device 16, heat may also be generated in implantable medical device 16 in surrounding tissue of patient 18. Such heat buildup in tissue of patient 18, beyond certain limits, is undesirable and should be limited as acceptable values. Generally, it is preferable to limit the temperature of external antenna 52 to not more than forty-one degrees Centigrade (41° C.) and to limit the temperature of implanted medical device 16 and the skin of patient 18 to thirty-nine degrees Centigrade (39° C.). In order to ensure that implantable medical device 16 is less than the upper limit of thirty-nine degrees Centigrade (39° C.), the actual temperature of external antenna 52 may be less than thirty-nine degrees Centigrade (39° C.). In general, the temperature of external antenna 52 may be maintained to be less than or equal to the desired maximum temperature of implanted medical device 16. While the temperature limits discussed above are anticipated under current conditions and regulations, it is recognized and understood that conditions and regulations may change or be different in different circumstances. Accordingly, the actual temperatures and temperature limits may change. Such temperature limits may be under software control in charging unit 50 so that any such temperatures or temperature limits can be modified to fit the then current circumstances.

Magnetic shield 36 serves to at least partially protect the portion of implantable medical device 16 contained within titanium housing 32 from the effects of energy transfer from external charging device 48 produced through inductive coupling from primary coil 54. Magnetic shield 36 is constructed of Metglas magnetic alloy 2714A (cobalt-based) manufactured by Honeywell International, Conway, S.C. Magnetic shield 36 is positioned between secondary coil 34 and housing 32 of implantable medical device 16 with secondary coil 34 facing cutaneous boundary 38. Magnetic shield does not interfere with the operation of secondary coil 34 because magnetic shield 36 is positioned away from primary coil 54. Also, magnetic shield does not interfere with telemetry between implantable medical device 16 and an external programmer because magnetic shield 36 is smaller than internal telemetry coil 44. That is, internal telemetry coil 44 lies outside of magnetic shield 36.

However, the material of magnetic shield 36 substantially limits the electromagnetic energy induced by primary coil 54 from penetrating beyond magnetic shield. Electromagnetic waves induced by primary coil 54 that reach titanium housing 32 will tend to be absorbed by titanium housing 54 and its components and will tend to cause the temperature of titanium housing 54 to rise. As the temperature of titanium housing 54 rises, such temperature increase will be disadvantageously transferred to the surrounding tissue of patient 18.

However, any electromagnetic waves which are prevented from reaching titanium housing 32 will not cause such a temperature rise.

Thermally conductive material 62 of external antenna 52 is positioned to contact the skin of patient 18 when external antenna 52 is placed for energy transfer, or charging, of implanted medical device 16. Thermally conductive material 62 tends to spread any heat generated at the skin surface and spread any such heat over a larger area. Thermally conductive material 62 tends to make the temperature of the skin surface more uniform than would otherwise be the case. Uniformity of temperature will tend to limit the maximum temperature of any particular spot on the skin surface. The skin itself is a pretty good conductor of heat and initially spreading any heat generated over a larger area of the skin will further assist the skin in dissipating any heat build-up on to surrounding tissue and further limit the maximum temperature of any particular location on the surface of the skin.

Thermally conductive material 62 is molded into the surface of external antenna 52 which will contact the skin surface of patient 18 when external antenna 52 provides energy transfer to implanted medical device 16. Since thermally conductive material 62 should pass electromagnetic energy from primary coil 54, thermally conductive material 62 should be constructed from a non-magnetic material. It is desirable that thermally conductive material 62 have a thermal conductivity of approximately 5.62 BTU inch/hour feet$^2$ degrees Fahrenheit (0.81 W/meters degrees Kelvin). Thermally conductive material may be constructed from a proprietary composite of approximately forty percent (40%) graphite, seven percent (7%) glass in RTP 199×103410 A polypropylene, manufactured by RTP Company, Winona, Minn. Thermally conductive material may not be electrically conductive in order to reduce eddy currents. Thermally conductive material may have a volume resistivity of approximately $10^3$ ohm-centimeters and a surface resistivity of $10^5$ ohms per square.

Energy absorptive material 62 can be placed in and/or around primary coil 54 of external antenna 52 in order to absorb some of the energy generated by primary coil 54. Energy absorptive material 62 may fill in an otherwise empty space of rotating core cup assembly 92. Heat generated by energy produced by primary coil 54 which is not effectively inductively coupled to secondary coil 34 will tend to cause a temperature rise in other components of external antenna 52 and, possibly, the skin of patient 18. At least a portion of this temperature rise can be blocked through the use of energy absorptive material 62. Energy absorptive material 62 is chosen to absorb heat build-up in surrounding components and tend to limit further temperature increases. Preferably, energy absorptive material 62 is selected to be material which undergoes a state change at temperatures which are likely to be encountered as the temperature of surrounding components rises during energy transfer, e.g., charging, using external antenna 52.

If it is a goal to limit the temperature of the skin of patient 18 to thirty-nine degrees Centigrade (39° C.), it is desirable to use of energy absorptive material 62 which has a state change at or near the temperature limit. In this example, the use of an energy absorptive material 62 having a state change in temperature area just below thirty-nine degrees Centigrade (39° C.), preferably in the range of thirty-five degrees Centigrade (35° C.) to thirty-eight degrees Centigrade (38° C.), can help limit the rise in the temperature of the skin of patient 18 to no more than the desired limit, in this example, thirty-nine degrees (39° C.).

As the temperature of surrounding components of external antenna 52 rise to a temperature which is just below the temperature at which energy absorptive material 62 changes state, at least a portion of further heat energy generated by primary coil 54 and surrounding components of external antenna 52 will go toward providing the energy necessary for energy absorptive material 62 to change state. As energy absorptive material 62 is in the process of changing state, its temperature is not increasing. Therefore, during the state change of energy absorptive material 62, energy absorptive material 62 is serving to at least partially limit a further rise in the temperature of components of external antenna 52. As the state change temperature of energy absorptive material has been preferably selected to be near or just below the temperature limit of the skin of patient 18, energy absorptive material 62 will tend to limit the temperature components of external antenna 52 from reaching the temperature limit and, hence, will also tend to limit the temperature of the skin of patient 18 from reaching the maximum desired temperature limit.

Energy absorptive material 62 may be constructed from wax and, in particular, a wax which has change of state temperature of approximately the maximum temperature at which external antenna 52 is desired to reach, such as thirty-eight (38) or thirty-nine (39) degrees Centigrade. Thus, the wax material of which energy absorptive material is constructed may melt at that temperature.

Inductive coupling between primary coil 54 of external antenna 52 and secondary coil of implantable medical device 16 is accomplished at a drive, or carrier, frequency, $f_{carrier}$, in the range of from eight (8) to twelve (12) kiloHertz. The carrier frequency, $f_{carrier}$, of external antenna 54 is approximately nine (9) kiloHertz unloaded.

However, the inductive coupling between primary coil 54 of external antenna 52 and secondary coil 34 of implantable medical device is dependent upon the mutual inductance between the devices. The mutual inductance depends upon a number of variables. Primary coil 54 is preferably made from a coil of wire that has an inductance L and a series or parallel tuned capacitance C. The values of both inductance L and capacitance C are fixed. For instance, if the desired drive frequency, $f_{carrier}$, of the energy transfer system was to be 1 megaHertz and external antenna 52 had an independence of one microHenry, capacitance would be added so that the resonant frequency of the energy transfer system would equal that of the drive frequency, $f_{carrier}$. The total capacitance added can be found using the equation $f_{resonate}$ equals one divided by two times pi ($\pi$) times the square root of L times C where L is the inductance of the energy transfer system. In this example, the value of capacitance C required to tune external antenna 52 to resonate at the carrier frequency of 1 megaHertz is calculated as approximately 25 nanofarads.

However, when the electrical properties of external antenna 52 change, either by the reflected environment or due to a physical distortion or change in the composition of the external antenna 52, the inductance, L, may be altered. The inductance, L, can be altered because it is made up of two separate parts. The first part is the self-inductance, $L_{self}$, of external antenna 52 at $f_{carrier}$. The second part is the mutual inductance, $L_{mutual}$, which is a measure of the change in current driving external antenna 52 and the magnetic effect, or "loading", which the environment has on external antenna 52. When the electrical characteristics of the environment of external antenna 52 change, $L_{self}$ remains constant while $L_{mutual}$ varies. The effect of a change in the overall inductance, whether that change is from $L_{self}$ or from $L_{mutual}$, is a change in the resonant frequency, $f_{resonate}$. Since C was chosen in order to have the resonant frequency, $f_{resonate}$, match the drive frequency, $f_{carrier}$, in order to increase the efficiency of energy transfer from primary coil 54 of external antenna 52 to secondary coil 34, a change in either or can result in the resonant frequency, $f_{resonate}$, being mismatched with the drive frequency, $f_{carrier}$. The result can be a less than optimum efficiency of energy transfer to implantable medical device 16.

As the drive frequency, $f_{carrier}$, varies with respect to the resonant frequency, $f_{resonate}$, apparent impedance of the energy transfer system, as seen by primary coil 54, will vary. The apparent impedance will be at a minimum when the drive frequency, $f_{carrier}$, exactly matches the resonant frequency, $f_{resonate}$. Any mismatch of the drive frequency, $f_{carrier}$, from the resonant frequency, will cause the impedance to increase. Maximum efficiency occurs when the drive frequency, $f_{carrier}$, matches the resonant frequency, $f_{resonate}$.

As the impedance of the energy transfer system varies, so does the current driving primary coil 54. As the impedance of the energy transfer system increases, the current driving primary coil 54 will decreases since the voltage being applied to primary coil 54 remains relatively constant. Similarly, the current driving primary coil 54 will increase as the impedance of the energy transfer system decreases. It can be seen then that point of maximum current driving primary coil 54 will be at a maximum when the impedance of the energy transfer system is at a minimum, when the resonant frequency, $f_{resonate}$, matches the drive frequency, $f_{carrier}$, and when maximum efficiency occurs.

The impedance of the energy transfer system can be monitored since the current driving primary coil 54 varies as a function of drive frequency, $f_{carrier}$. The drive frequency can be varied and the current driving primary coil can be measured to determine the point at which the impedance of the energy transfer system is at a minimum, the resonant frequency, $f_{resonate}$, matches the drive frequency, $f_{carrier}$, and when maximum efficiency occurs.

Instead of holding the drive frequency, $f_{carrier}$, constant for a nominal resonant frequency, $f_{resonate}$, the drive frequency, $f_{carrier}$, may be varied until the current driving primary coil 54 is at a maximum. This is not only the point at which the impedance of the energy transfer system is at a minimum but also the point at which maximum efficiency occurs.

Maximum efficiency is not as important in systems, such as telemetry systems, which are utilized in a static environment or for relatively short periods of time. In a static environment, the resonant frequency, $f_{resonate}$, may be relatively invariable. Further, efficiency in not terribly important when energy or information transfer occurs over a relatively short period of time.

However, transcutaneous energy transfer systems can be utilized over extended periods of time, either to power the implanted medical device 16 over an extended period of time or to charge a replenishable power supply within implanted medical device 16. Depending upon capacity of the replenishable power supply and the efficiency of energy transfer, charging unit 50 can be utilized for hours and typically can be used as patient 18 rests or over night as patient 18 sleeps. Further, over the extended period of time in which charging unit 50 is utilized, external antenna 52 is affixed to the body of patient 18. As patient 18 attempts to continue a normal routine, such as by making normal movement or by sleeping, during energy transfer, it is difficult to maintain external antenna 52 in a completely fixed position relative to secondary coil 34. Movement of external antenna 52 with respect to secondary coil 34 can result in a change in mutual inductance, $L_{mutual}$, a change in impedance and a change in the resonant frequency, $f_{resonate}$. Further, any change in spatial positioning of the energy transfer system with any external conductive object, any change in the characteristics of external antenna 52, such as by fractures in magnetic core 58, for example, a change in the charge level of rechargeable power source 24 of implantable medical device 16 or a change in the power level of charging unit 50, all can result in a change of mutual inductance, $L_{mutual}$.

Drive frequency, $f_{carrier}$, may be varied, not only initially during the commencement of energy transfer, e.g., charging, but also during energy transfer by varying the drive frequency, $f_{carrier}$, in order to match the drive frequency, $f_{carrier}$, with the resonant frequency, $f_{resonate}$, and, hence, maintaining a relatively high efficiency of energy transfer. As an example, drive frequency, $f_{carrier}$, can be constantly updated to seek resonant frequency, $f_{resonate}$, or drive frequency, $f_{carrier}$, can be periodically updated, perhaps every few minutes or every hour as desired. Such relatively high efficiency in energy transfer will reduce the amount of time charging unit 50 will need to be operated, for a given amount of energy transfer, e.g., a given amount of battery charge. A reduced energy transfer, or charging, time can result in a decrease in the amount of heating of implanted medical device 16 and surrounding tissue of patient 18.

External charging device 48 may incorporate temperature sensor 87 in external antenna 52 and control circuitry in charging unit 50 which can ensure that external antenna 52 does not exceed acceptable temperatures, generally a maximum of thirty-eight degrees Centigrade (38° C.), preferably 38.3 degrees Centigrade. Temperature sensor 87 in external antenna 52 can be used to determine the temperature of external antenna 52. Temperature sensor 87 can be positioned in close proximity to thermally conductive material 62 in order to obtain reasonably accurate information on the temperature of the external surface of external antenna 52 contacting patient 18. Preferably, temperature sensor 87 is affixed to thermally conductive material 62 with a thermally conductive adhesive. Thermally conductive material 62 smoothes out any temperatures differences which otherwise might occur on the surface of external antenna 52 contacting patient 18. Positioning temperature sensor 87 in the proximity or touching thermally conductive material 62 enables an accurate measurement of the contact temperature.

Control circuitry using the output from temperature sensor 87 can then limit the energy transfer process in order to limit the temperature which external antenna 52 imparts to patient 18. As temperature sensor 87 approaches or reaches preset limits, control circuitry can take appropriate action such as limiting the amount of energy transferred, e.g., by limiting the current driving primary coil 54, or limiting the time during which energy is transferred, e.g., by curtailing energy transfer or by switching energy transfer on and off to provide an energy transfer duty cycle of less than one hundred percent.

When the temperature sensed by the temperature sensor is well below preset temperature limits, it may be acceptable to report the temperature with relatively less precision. As an example, if the temperature sensed by temperature sensor 87 is more than two degrees Centigrade (2° C.) away from a preset limit of thirty-eight degrees Centigrade (38° C.), it may be acceptable to know the temperature with an accuracy of three degrees Centigrade (3° C.).

However, when the temperature of external antenna 52 approaches to within two degrees Centigrade (2° C.), it may be desirable to know the temperature with a much greater accuracy, for example, an accuracy of within one tenth of one degree Centigrade (0.1° C.).

It is generally difficult, however, to produce a temperature which has a high degree of accuracy over a very broad temperature range. While a temperature sensor can easily be produced to provide a resolution within one-tenth of one degree Centigrade (0.1° C.) over a relatively narrow range temperatures, it can be difficult to produce a temperature sensor providing such a resolution over a broad range of temperatures.

A dual range temperature sensor has a first, broad, less accurate range of measurement from thirty degrees Centigrade (30° C.) to forty-two degrees Centigrade (42° C.) having an accuracy within three degrees Centigrade (3° C.). Further, this temperature sensor has a second, narrow, more accurate range of measurement over four degrees Centigrade (4° C.), from thirty-six degrees Centigrade (36° C.) to forty-two degrees Centigrade (42° C.), having an accuracy within one-tenth of one degree Centigrade (0.1° C.).

Figure 16:
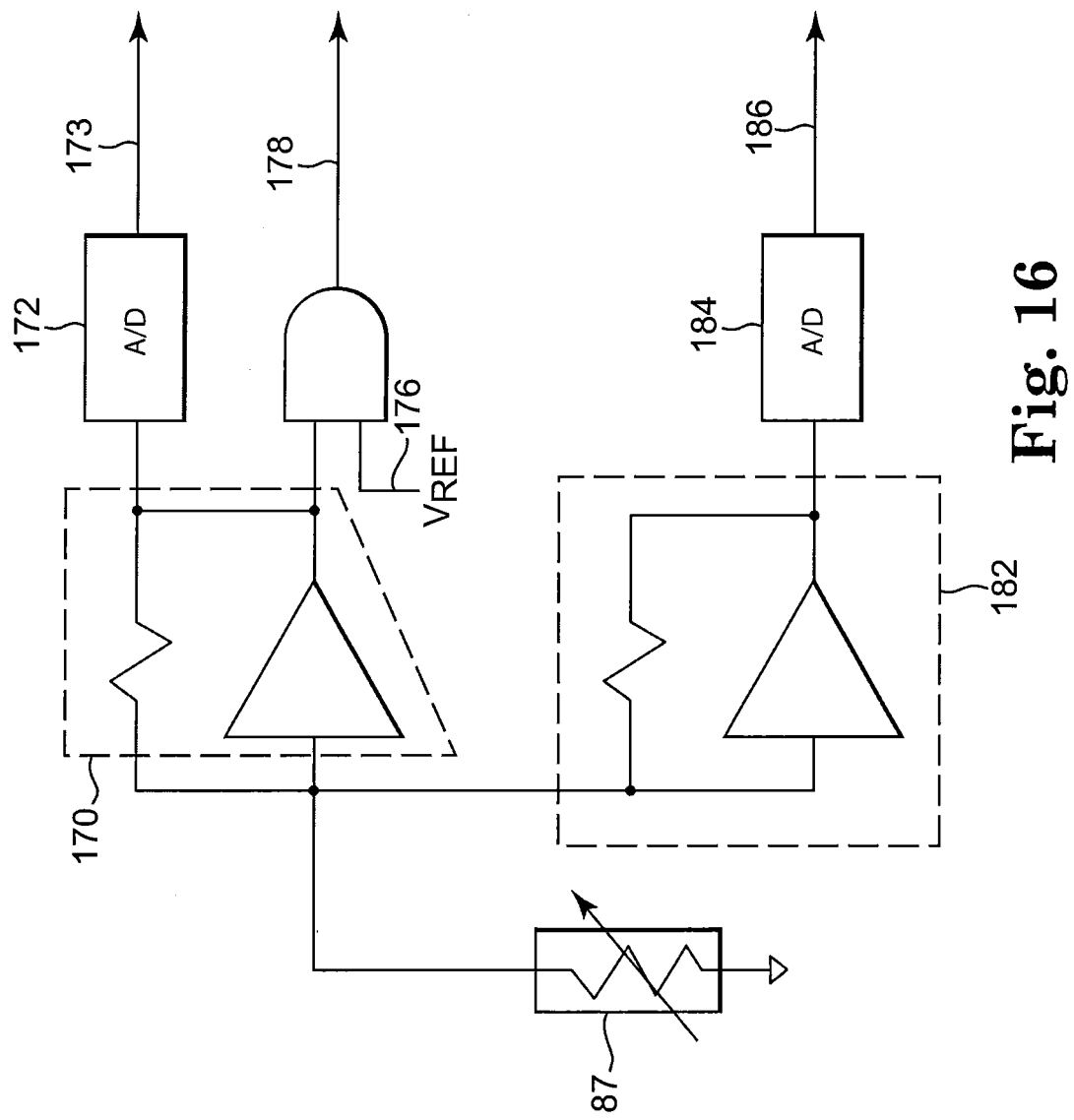
FIG. 16 is a schematic diagram of a dual range temperature sensor.

FIG. 16 illustrates a dual range temperature sensor utilizing temperature sensor 87. Temperature sensor 87, located in external antenna 52, is coupled to amplifier 170 which has been pre-calibrated to operate only in the range of from thirty degrees Centigrade (30° C.) to forty-two degrees Centigrade (42° C.). Components of amplifier 170 have an accuracy reflecting a temperature within one-tenth of one degree Centigrade (0.1° C.). The analog output of amplifier 170 is sent to analog-to-digital converter 172 producing a digital output 173 having an accuracy of one-tenth of one degree Centigrade (0.1° C.). The analog output of amplifier 170 could be also sent to comparator 174 which compares the analog output against a known reference voltage 176 which is set to at a predetermined level to produce a positive output 178 when temperature sensor 87 reflects a temperature of 38.3 degrees Centigrade, the maximum temperature permitted for external antenna 52. Control logic in charging unit 50 can then take appropriate action to limit further temperature increases such as by ceasing or limiting further energy transfer and/or charging. Temperature sensor 87 is also coupled to amplifier 182. Components of amplifier 182 have an accuracy reflecting a temperature within three degrees Centigrade (3° C.), much less accuracy than amplifier 170, but amplifier 182 can operate over the much larger temperature range of zero degrees Centigrade (0° C.) to forty-five degrees Centigrade (45° C.). The output of amplifier 182 is sent to analog-to-digital converter 184 producing a digital output 186 having an accuracy of three degrees Centigrade (3° C.).

Figure 17:
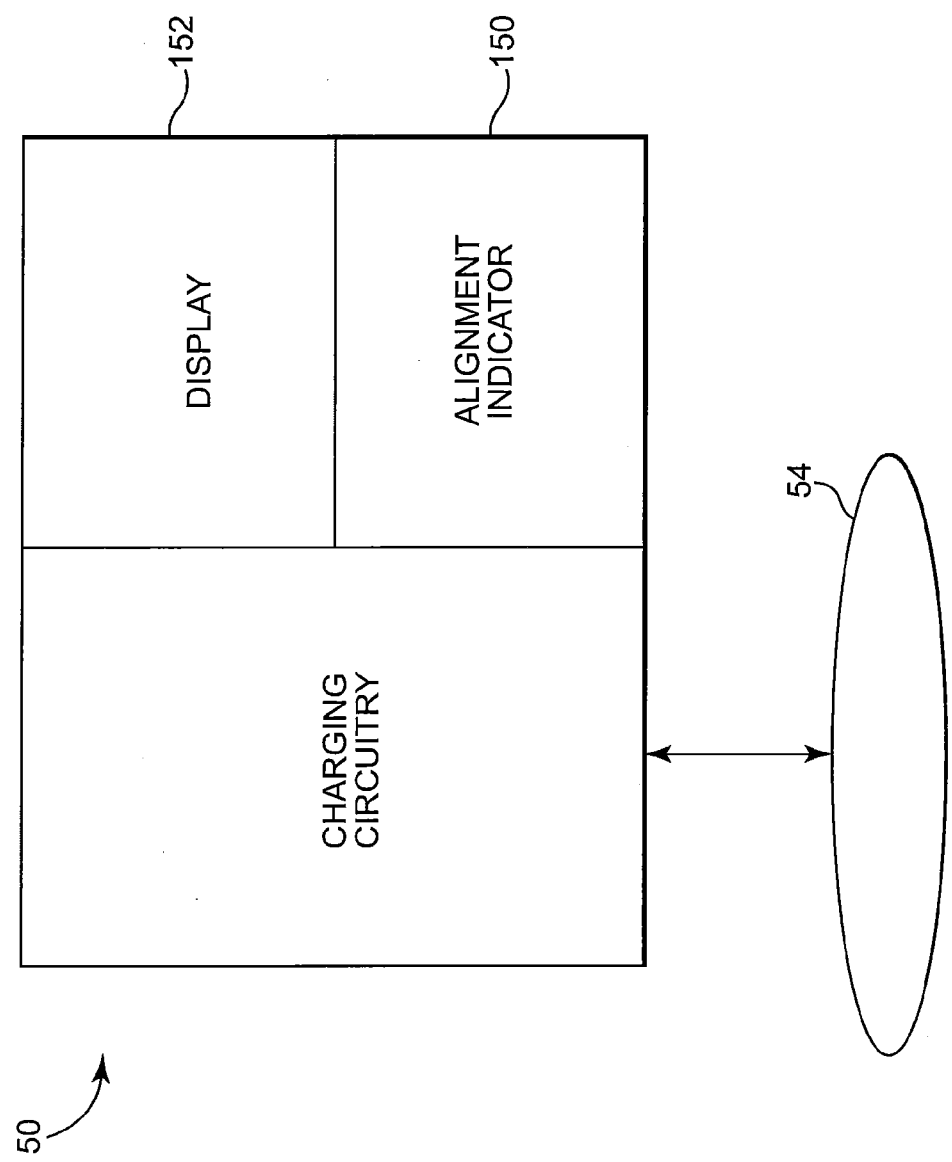
FIG. 17 is a block diagram of an alignment indicator.

FIG. 17 illustrates a functional block diagram of a preferred embodiment of charging unit 50 incorporating alignment indicator 150 and display 152. During the process in which rechargeable power source 24 is charged through the use of charging unit 50, it is desirable to obtain the efficiency in power transfer from external charging unit 50 and rechargeable power source 24. Typically, efficiency of energy transfer will be greatest when primary coil 54 of charging unit 50 is transcutaneously optimally aligned with secondary coil 34 of implantable medical device 16. The subcutaneous position of implantable medical device can often be discerned by a tell-tale bulge in cutaneous 38 and such bulge can be used as a guide in placement of primary coil 54. However, secondary coil 34 may not be centered with respect to implantable medical device 16 and/or such bulge. Similarly, primary coil may be centered in charging unit 50 or external antenna 52. Thus, it can be difficult to determine that optimum position for placement of primary coil 54 by using the physical housing of charging unit 50 or external antenna 52 in conjunction with a bulge created by the implanted device.

In a preferred embodiment, alignment indicator 150 functionally provides active feedback to patient 18, or other person, responsible for positioning primary coil 54 during charging of rechargeable power source 24. Alignment may provide sensory feedback, e.g., audible, visual or tactile. In a preferred embodiment, display 152 is utilized to alert a user positioning primary coil 54. In a preferred embodiment, display 152 is a series of lights forming a bar graph indicative of a degree of efficiency of energy transfer, i.e., alignment.

Figure 18:
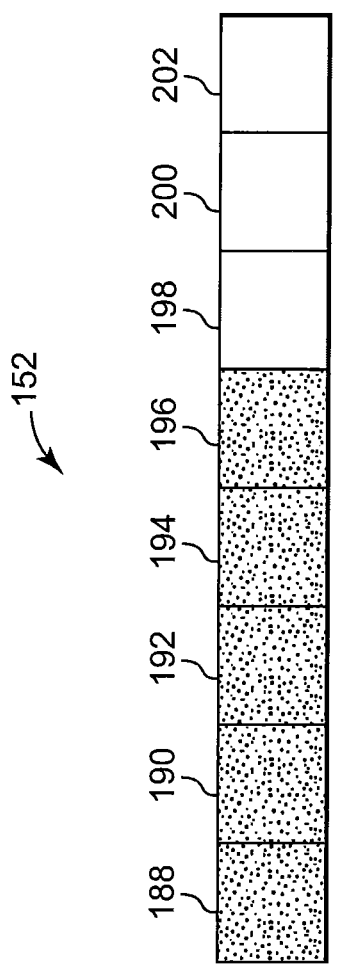
FIG. 18 is a diagram of a display for the alignment indicator of FIG. 17.

A preferred embodiment of display 152 is represent by bar graph 154, illustrated in FIG. 18. Bar graph 154 consists of eight (8) lights, namely light 188, light 190, light 192, light 194, light 196, light 196, light 198, light 200 and light 202, arranged in a row such that when one or more lights are lit starting at one end of bar graph 154, the visual appearance of the series of lights resembles a bar graph. In the example illustrated in FIG. 18, five (5) of the lights of bar graph 154 are illuminated, namely light 188, light 190, light 192, light 194, light 196, giving a visual indication of the alignment of primary coil 54 to secondary coil 34. Lights 198, 200 and 202 are not illuminated since the degree of alignment required to achieve such an indication is not present. It is to be recognized and understood that the representation of five (5) lights lit in bar graph 154 is merely example and other numbers of lights, including no lights or all lights, being lit could be representative of a degree of alignment.

In a preferred embodiment, Table 4 provides an illustration of how the number of lights, representing a bar, may be lit depending upon a function of the current associated with, or through, secondary coil 34. In this example, the calculated efficiency of energy transfer is used. Efficiency of energy transfer in this embodiment is defined as described above with reference to FIG. 14. Table 4 also provides an indication of an approximate amount of time that would be required for complete recharging of rechargeable power source 24 at the indicated alignment.

TABLE 4

| Efficiency | | Number of Lights | Current | Time |
| --- | --- | --- | --- | --- |
| Zero | 5.6% | 0 | 14 mA | 18 hours |
| 5.6% | 6.4% | 1 | 16 mA | 16 hours |
| 6.4% | 7.2% | 2 | 18 mA | 14 hours |
| 7.2% | 8.0% | 3 | 20 mA | 12 hours |
| 8.0% | 10.0% | 4 | 25 mA | 10 hours |
| 10.0% | 12.4% | 5 | 31 mA | 8 hours |
| 12.4% | 14.8% | 6 | 37 mA | 7 hours |
| 14.8% | 17.5% | 7 | 44 mA | 6 hours |
| 17.5% | maximum | 8 | >44 mA | <6 hours |

While display 152 has been illustrated and described as a bar graph 154 represented by a series of lights, it is to be recognized and understood that other forms of display are contemplated, including, but not limited to, LED displays, LCD displays, plasma displays, numeric or alpha-numeric displays, and the like. Any form of visual representation of the amount of current associated with secondary coil 34 and/or the efficiency of energy transfer can suffice.

It is also to be recognized and understood, while the indication of alignment has been described and illustrated as a visual indication, that other forms of indication are also contemplated. For example, the indication could be audible, represented by a tone that changes volume and/or pitch as alignment changes. Further, such an audible indication could be verbal. In addition, it is contemplated that tactile indications are contemplated. For example, a vibration that varies in intensity and/or frequency could be used to indicate change in alignment. The indication of alignment could be anything that can be detected to the sensory perception of a person.

In a preferred embodiment, the alignment indication is based upon the amount of current actually flowing through rechargeable power source 24. It is to be recognized and understood, however, that it is not necessary that the current measured actually be the current passing through rechargeable power source 24. Alternatively, an alignment measurement may be made by measuring a value, e.g., current or voltage, associated with, e.g., proportional to, the current passing through rechargeable power source 24. It is significant, however, that the current measurement be taken on the implant side of the charging system so that the measurement of alignment provides an actual indication of alignment and not a presumed alignment based upon an external measurement.

As rechargeable power source 24 is charged and the voltage across rechargeable power source 24 approaches its fully recharged value, it becomes more difficult to ascertain when alignment is obtained. This is due, in part, to relatively small changes in the values of the charging current as a fully charged state is approached. Partly, because of this reason and partly because current levels and power levels are lower as a fully charged state is approached, it may be desirable to discontinue alignment indication following reaching a predetermined point in the charging cycle. For example, the alignment indication system could cease to report alignment when the voltage across rechargeable power source 24 reaches ninety percent (90%) of expected fully charged state of rechargeable power source 24.

Figure 19:
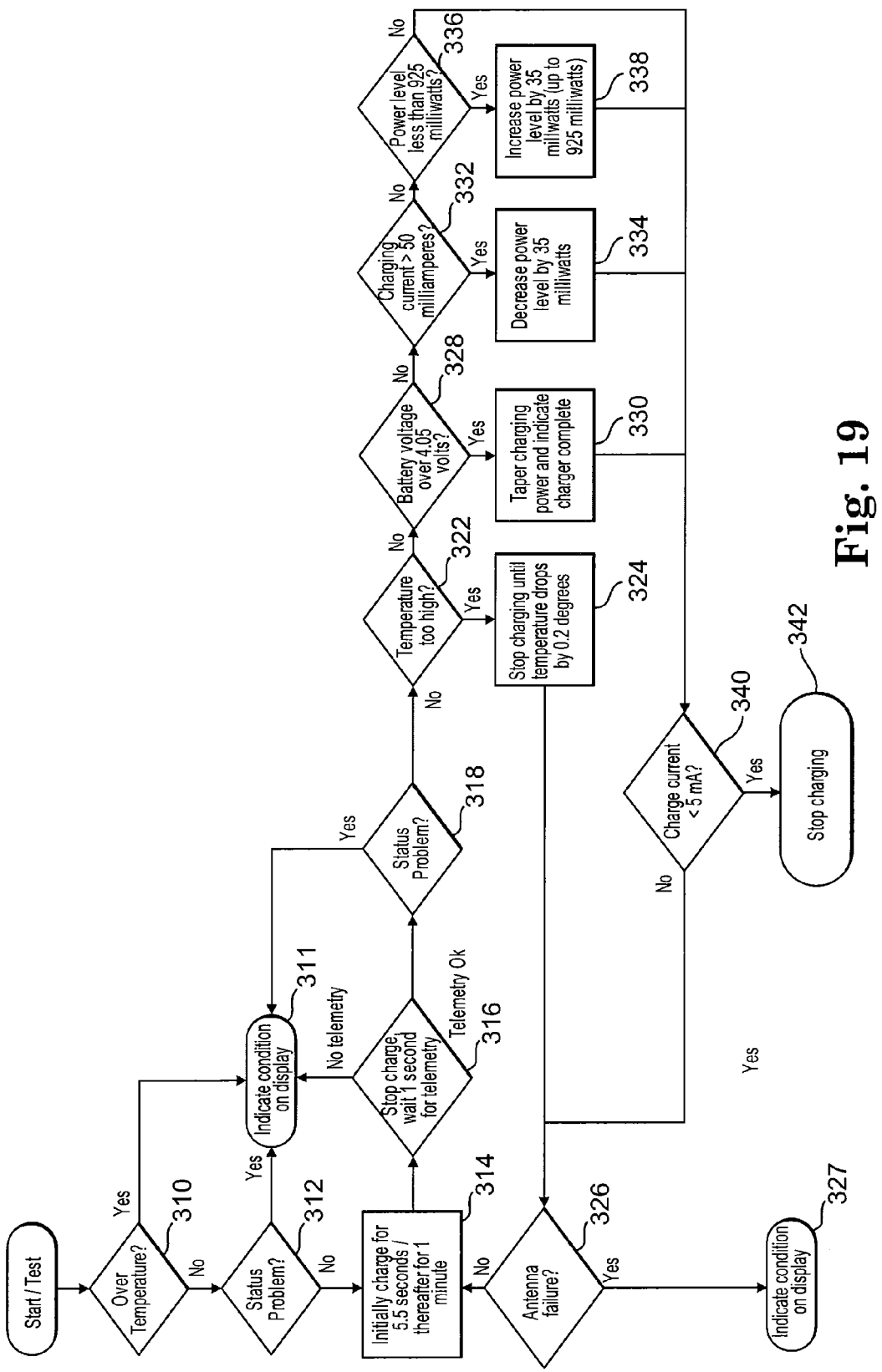
FIG. 19 is a flow chart illustrating charging of an implantable medical device.

Operation of charging unit 50, including alignment indicator 150, is illustrated in the flow chart of FIG. 19. First, charging unit 50 determines (310) whether external antenna 52 is over the temperature limit set for charging operation. This temperature limit can help prevent patient 18 from being exposed to temperatures that are higher than desired. If external antenna 52 of charging unit 50 is over temperature, an alert condition is indicated (311). If external antenna is not over the temperature limit, charging unit 50 then checks (312) for a status problem with charging unit 50. If a status problem is found, an alert condition is indicated (311).

If a status problem is not found, charging unit 50 initially charges (314) rechargeable power source 24 of implantable medical device 16 for 5.5 seconds. Charging unit 50 then stops charging and waits (316) one second to check for reception of a telemetry signal from implantable medical device 16. An example of information sent from implantable medical device 16 to charging unit 50 via telemetry can include the value of a current associated with secondary coil 34, e.g., the value of the current flowing through secondary coil 34. If no telemetry signal is detected, an alert condition is indicated (311). If telemetry is received, charging unit 50 then checks (318) for a status problem with implantable medical device 16. If a status problem is detected, an alert condition is indicated (311).

If no status problem exists, charging unit 50 checks (322) to determine if the temperature is too high. Again, a temperature exceeding predetermined limits is not advantageous. If an over temperature condition is detected, charging is stopped and a status indication is displayed until the temperature drops below a predetermined level.

If no over temperature condition exists, charging unit 50 checks (328) to determine if the voltage across rechargeable power source 24 is over a voltage at which the charging rate should begin to decrease, e.g., 4.05 volts. If the voltage across rechargeable power 24 is greater than 4.05 volts, then charging unit 50 begins to taper charging power (330).

If the voltage across rechargeable power source 24 is not over 4.05 volts, charging unit 50 checks (332) to determine whether the charging current through rechargeable power source 24 is over a current rate that is not desirable, e.g., 50 milliamperes. If the charging current is over 50 milliamperes, then the charging power level is decreased (334) by an appropriate, e.g., by 35 milliwatts.

If the charging current is not over 50 milliamperes, charging unit 50 checks (336) to determine if the charging power level is less than appropriate amount, e.g., 925 milliwatts. If the power level is less than 925 milliwatts, the charging power level is increased (338) by 35 milliwatts, up to a maximum of 925 milliwatts.

If the charge current is below (340) five (5) milliamperes, then charging unit 50 stops (342) charging and indicates that charging is complete, e.g., by lighting the charging complete indicator light.

If not, charging unit 50 then charges (314) rechargeable power source for one (1) minute and then conducts the aforementioned tests, checks and actions as performed after the initial 5.5 second charge.

Thus, embodiments of the alignment indication for transcutaneous energy transfer are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for transcutaneous energy transfer, comprising:
   an implantable medical device having componentry for providing a therapeutic output, said implantable medical device having an internal power source and a secondary coil operatively coupled to said internal power source, said implantable medical device adapted to be implanted in a patient; and
   an external power source having a primary coil, said external power source providing energy to said implantable medical device when said primary coil of said external power source is placed in proximity of said secondary coil of said implantable medical device and thereby generating a current, having a value, passing through said internal power source:
   wherein said external power source automatically varies its power output based on a value associated with said current passing through said internal power source;
   wherein said external power source automatically varies its power output based on a measured current associated with said current passing through said internal power source.

2. A system for transcutaneous energy transfer, comprising:
   an implantable medical device having componentry for providing a therapeutic output, said implantable medical device having an internal power source and a secondary coil operatively coupled to said internal power source, said implantable medical device adapted to be implanted in a patient; and
   an external power source having a primary coil, said external power source providing energy to said implantable medical device when said primary coil of said external power source is placed in proximity of said secondary coil of said implantable medical device and thereby generating a current, having a value, passing through said internal power sources;
   wherein said external power source automatically varies its power output based on a value associated with said current passing through said internal power source;
   wherein said current passing through said internal power source declines as said voltage of said internal power source increases during a charging cycle.

3. A system for transcutaneous energy transfer, comprising:
- an implantable medical device having componentry for providing a therapeutic output, said implantable medical device having an internal power source and a secondary coil operatively coupled to said internal power source, said implantable medical device adapted to be implanted in a patient; and
- an external power source having a primary coil, said external power source providing energy to said implantable medical device when said primary coil of said external power source is placed in proximity of said secondary coil of said implantable medical device and thereby generating a current, having a value, passing through said internal power source;
- wherein said external power source automatically varies its power output based on a value associated with said current passing through said internal power source;
- wherein said current passing through said internal power source comprises a maximum amount of current for charging said internal power source;
- wherein said current passing through said internal power source declines over time as an internal impedance of said internal power source increases.

4. A system for transcutaneous energy transfer, comprising:
- an implantable medical device having componentry for providing a therapeutic output, said implantable medical device having an internal power source and a secondary coil operatively coupled to said internal power source, said implantable medical device adapted to be implanted in a patient; and
- an external power source having a primary coil, said external power source providing energy to said implantable medical device when said primary coil of said external power source is placed in proximity of said secondary coil of said implantable medical device and thereby generating a current, having a value, passing through said internal power source;
- wherein said external power source automatically varies its power output based on a value associated with said current passing through said internal power source;
- wherein said external power source terminates its power output if said current passing through said internal power source is below a minimum amount.

5. An external power source for use with an implantable medical device adapted to be implanted in a patient and having componentry for providing a therapeutic output, an internal power source and a secondary coil operatively coupled to said internal power source, comprising:
- an external power unit; and
- a primary coil, operatively coupled to said external power unit;
- said external power unit providing energy to said implantable medical device when said primary coil is placed in proximity of said secondary coil of said implantable medical device and thereby generating a current having a value passing through said internal power source;
- wherein said external power source automatically varies its power output based on a value associated with said current passing through said internal power source;
- wherein said external power source automatically varies its power output based on a measured current associated with said current passing through said internal power source.

6. An external power source for use with an implantable medical device adapted to be implanted in a patient and having componentry for providing a therapeutic output, an internal power source and a secondary coil operatively coupled to said internal power source, comprising:
- an external power unit; and
- a primary coil, operatively coupled to said external power unit;
- said external power unit providing energy to said implantable medical device when said primary coil is placed in proximity of said secondary coil of said implantable medical device and thereby generating a current having a value passing through said internal power source;
- wherein said external power source automatically varies its power output based on a value associated with said current passing through said internal power source;
- wherein said current passing through said internal power source declines as said voltage of said internal power source increases during a charging cycle.

7. An external power source for use with an implantable medical device adapted to be implanted in a patient and having componentry for providing a therapeutic output, an internal power source and a secondary coil operatively coupled to said internal power source, comprising:
- an external power unit; and
- a primary coil, operatively coupled to said external power unit;
- said external power unit providing energy to said implantable medical device when said primary coil is placed in proximity of said secondary coil of said implantable medical device and thereby generating a current having a value passing through said internal power source;
- wherein said current passing through said internal power source comprises a maximum amount of current for charging said internal power source;
- wherein said external power source automatically varies its power output based on a value associated with said current passing through said internal power source
- wherein said current passing through said internal power source declines over time as an internal impedance of said internal power source increases.

8. An external power source for use with an implantable medical device adapted to be implanted in a patient and having componentry for providing a therapeutic output, an internal power source and a secondary coil operatively coupled to said internal power source, comprising:
- an external power unit; and
- a primary coil, operatively coupled to said external power unit;
- said external power unit providing energy to said implantable medical device when said primary coil is placed in proximity of said secondary coil of said implantable medical device and thereby generating a current having a value passing through said internal power source;
- wherein said external power source automatically varies its power output based on a value associated with said current passing through said internal power source;
- wherein said external power source terminates its power output if said current passing through said internal power source is below a minimum amount.

9. A method of transcutaneous energy transfer between an external primary coil and an inductively coupled secondary coil of an implanted medical device, said external primary coil being operatively coupled to a charging unit, said secondary coil supplying power to an internal power source of said implanted medical device, said internal power source having an internal impedance, comprising the steps of:

driving said external primary coil with a charging signal from said charging unit generating a current passing through said internal power source; and said charging unit automatically varying its power output based on a value associated with said current passing through said internal power source;

wherein said automatically varying step automatically varies its power output based on a measured current associated with said current passing through said internal power source.

10. A method of transcutaneous energy transfer between an external primary coil and an inductively coupled secondary coil of an implanted medical device, said external primary coil being operatively coupled to a charging unit, said secondary coil supplying power to an internal power source of said implanted medical device, said internal power source having an internal impedance, comprising the steps of:

driving said external primary coil with a charging signal from said charging unit generating a current passing through said internal power source; and said charging unit automatically varying its power output based on a value associated with said current passing through said internal power source;

wherein said current passing through said internal power source declines as said voltage of said internal power source increases during a charging cycle.

11. A method of transcutaneous energy transfer between an external primary coil and an inductively coupled secondary coil of an implanted medical device, said external primary coil being operatively coupled to a charging unit, said secondary coil supplying power to an internal power source of said implanted medical device, said internal power source having an internal impedance, comprising the steps of:

driving said external primary coil with a charging signal from said charging unit generating a current passing through said internal power source; and said charging unit automatically varying its power output based on a value associated with said current passing through said internal power source;

wherein said current passing through said internal power source comprises a maximum amount of current for charging said internal power source;

wherein said current passing through said internal power source declines over time as an internal impedance of said internal power source increases.

12. A method of transcutaneous energy transfer between an external primary coil and an inductively coupled secondary coil of an implanted medical device, said external primary coil being operatively coupled to a charging unit, said secondary coil supplying power to an internal power source of said implanted medical device said internal power source having an internal impedance, comprising the steps of:

driving said external primary coil with a charging signal from said charging unit generating a current passing through said internal power source; and said charging unit automatically varying its power output based on a value associated with said current passing through said internal power source;

wherein said external power source terminates its power output if said current passing through said internal power source is below a minimum amount.

* * * * *